United States Patent [19]
Shaffer et al.

[11] Patent Number: 5,335,650
[45] Date of Patent: Aug. 9, 1994

[54] PROCESS CONTROL FOR LIQUID VENTILATION AND RELATED PROCEDURES

[75] Inventors: Thomas H. Shaffer, Lansdown; Marla R. Wolfson, Philadelphia, both of Pa.

[73] Assignee: Temple University - Of The Commonwealth System of Higher Education, Pa.

[21] Appl. No.: 960,611

[22] Filed: Oct. 13, 1992

[51] Int. Cl.$^5$ .................................... A61M 16/00
[52] U.S. Cl. ..................... 128/200.24; 128/913; 128/898; 604/49
[58] Field of Search ............ 128/200.24, 204.23, 128/913, 716, 720, 725, 898; 604/20, 22, 49, 24; 514/23

[56] References Cited

U.S. PATENT DOCUMENTS

| | | | |
|---|---|---|---|
| 3,251,361 | 5/1966 | Rusz | 128/200.11 |
| 4,232,665 | 11/1980 | Vaseen | 128/200.24 |
| 4,361,138 | 11/1982 | Kinoshita | 128/4 |
| 4,378,797 | 4/1983 | Osterholm | 604/24 |
| 4,393,863 | 7/1983 | Osterholm | 604/28 |
| 4,401,431 | 8/1983 | Arp | 604/4 |
| 4,444,201 | 4/1984 | Itoh | 128/716 |
| 4,445,500 | 5/1984 | Osterholm | 604/28 |
| 4,445,514 | 5/1984 | Osterholm | 128/632 |
| 4,445,515 | 5/1984 | DiResta | 128/632 |
| 4,445,886 | 5/1984 | Osterholm | 604/28 |
| 4,445,887 | 5/1984 | Osterholm | 604/28 |
| 4,445,888 | 5/1984 | Osterholm | 604/28 |
| 4,446,154 | 5/1984 | Osterholm | 514/10 |
| 4,446,155 | 5/1984 | Osterholm | 514/10 |
| 4,450,841 | 5/1984 | Osterholm | 128/632 |
| 4,451,251 | 5/1984 | Osterholm | 604/24 |
| 4,464,169 | 8/1984 | Semm | 604/26 |
| 4,477,395 | 10/1984 | Albarda | 261/131 |
| 4,481,944 | 11/1984 | Bunnell | 128/204.18 |
| 4,484,576 | 11/1984 | Albarda | 128/202.22 |
| 4,564,748 | 1/1986 | Gupton | 219/497 |
| 4,585,007 | 4/1986 | Uchigaki et al. | 128/632 |

(List continued on next page.)

FOREIGN PATENT DOCUMENTS

| | | |
|---|---|---|
| 2454330 | 5/1975 | Fed. Rep. of Germany ............ 128/204.23 |
| 8801323 | 12/1989 | Netherlands . |
| 858824 | 8/1981 | U.S.S.R. . |

OTHER PUBLICATIONS

F. Gollan et al, "Compliance and Diffusion During Respiration with Fluorocarbon Fluid", Federation Proceedings Sep.–Oct. 1970, V. 29, #5, pp. 1725–1730.

(List continued on next page.)

*Primary Examiner*—Edgar S. Burr
*Assistant Examiner*—Eric P. Raciti
*Attorney, Agent, or Firm*—Seidel, Gonda, Lavorgna & Monaco

[57] ABSTRACT

A process is provided for controlling a ventilation procedure wherein a liquid ventilation system passes a breathing liquid through at least a portion of a patient's pulmonary pathways. In this process, desired ranges for certain process parameters associated with the liquid ventilation system are established. These desired ranges are input into a central processing unit. Initial settings for the liquid ventilation system are then made such that the actual conditions which will initially occur during the liquid ventilation procedure fall within their respective desired ranges. Thereafter, the liquid ventilation procedure is commenced. During the liquid ventilation procedure, conditions which relate to the established ranges are continually monitored by appropriate sensors. The monitored information is also input into the central processing unit. The central processing unit is designed to compare the actually-occurring monitored conditions to their respective desired ranges and determine if there is a difference. If there is a difference, the central processing unit generates signals which are designed to correct the discrepancy. These signals can be designed to trigger alarms which instruct an operator to make the appropriate adjustments and/or to activate a servo-controlled valving network.

11 Claims, 12 Drawing Sheets

U.S. PATENT DOCUMENTS

| | | | |
|---|---|---|---|
| 4,587,966 | 5/1986 | Albarda | 128/202.22 |
| 4,657,532 | 4/1987 | Osterholm | 604/24 |
| 4,661,092 | 4/1987 | Popovich | 604/26 |
| 4,670,006 | 6/1987 | Sinnett et al. | 604/26 |
| 4,676,774 | 6/1987 | Semm et al. | 604/26 |
| 4,676,776 | 6/1987 | Howson | 604/31 |
| 4,686,085 | 11/1987 | Osterholm | 422/45 |
| 4,686,974 | 8/1987 | Sato et al. | 128/204.23 |
| 4,688,577 | 8/1987 | Bro | 128/670 |
| 4,708,831 | 11/1987 | Elsworth et al. | 261/130 |
| 4,717,548 | 1/1988 | Lee | 422/82.04 |
| 4,756,706 | 7/1988 | Kerns et al. | 604/66 |
| 4,758,431 | 7/1988 | Osterholm | 424/680 |
| 4,781,676 | 11/1988 | Schweighardt et al. | 604/21 |
| 4,795,423 | 1/1989 | Osterholm | 604/24 |
| 4,810,243 | 3/1989 | Howson | 604/31 |
| 4,830,849 | 5/1989 | Osterholm | 424/2 |
| 4,874,362 | 10/1989 | Wiest et al. | 604/26 |
| 4,889,116 | 12/1989 | Taube | 128/204.23 |
| 4,919,895 | 4/1990 | Heldebrandt et al. | 422/129 |
| 4,963,130 | 10/1990 | Osterholm | 604/24 |
| 4,966,578 | 10/1990 | Baier et al. | 604/26 |
| 4,972,842 | 11/1990 | Korten | 128/716 |
| 4,981,691 | 1/1991 | Osterholm et al. | 424/422 |
| 5,006,109 | 4/1991 | Douglas et al. | 604/26 |
| 5,097,424 | 3/1992 | Gwervi | 364/510 |
| 5,129,390 | 7/1992 | Chopin et al. | 128/204.21 |
| 5,158,536 | 10/1992 | Sekins | 604/20 |
| 5,188,098 | 2/1993 | Hoffman | 128/204.23 |

OTHER PUBLICATIONS

H. Rahn, "Discussion on Liquid Breathing", Federation Proceedings, Sep.–Oct. 1970, V. 29, #5, pp. 1753–1754.

D. Dundas, "Fluorocarbon Liquid Oxygenator", Federation Proceedings, Sep.–Oct. 1970, V. 29, #5, pp. 1771–1777.

W. Marsh et al, "A Flexible System for Closed-Loop Ventilator Development", Procdgs 14th Hawaii–Intl. Conf. on Sys. Sci., pp. 457–462, 1981.

Shaffer, et al., "An Electromechanical Demand Regulated Liquid Breathing System", *IEEE Translations on Biomedical Engineering*, vol. BME-22, No. 5, pp. 412–417 (Sep. 1975).

Moskowitz, "A Mechanical Respirator for Control of Liquid Breathing", *Federation Proceedings*, vol. 29, No. 5. pp. 1751–1752 (Sep.–Oct. 1970).

(LIQUID CONTROL SYSTEM)

(GAS CONTROL SYSTEM)

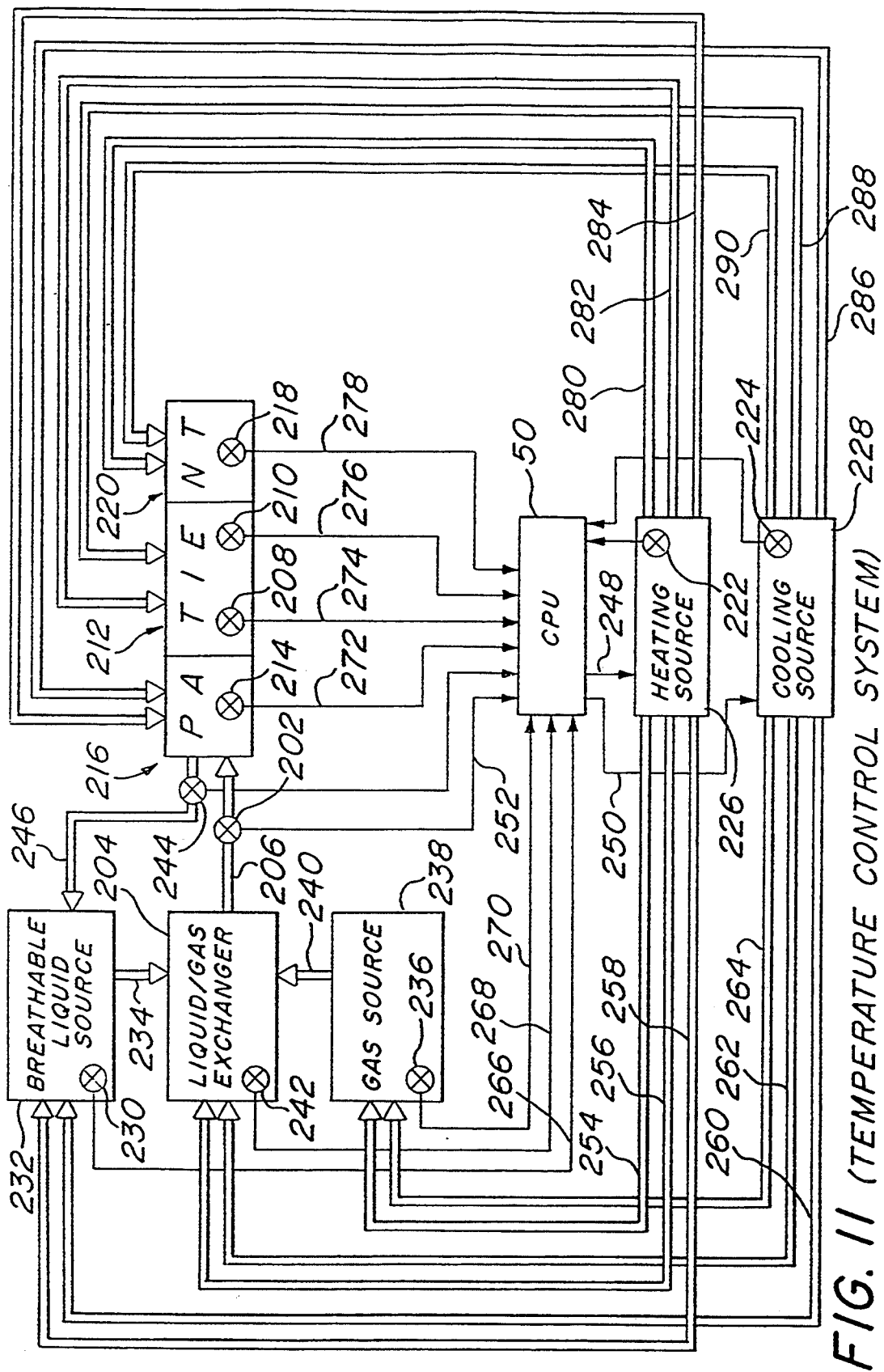
FIG. 11 (TEMPERATURE CONTROL SYSTEM)

PROCESS CONTROL FOR LIQUID VENTILATION AND RELATED PROCEDURES

FIELD OF THE INVENTION

This invention relates to methods and process control systems, for introducing breathable liquids into the pulmonary system of patients. These methods and process control systems are also useful as a means of delivering biological agents into a patient through the patient's pulmonary pathways and for controlling a patient's internal and/or external body temperatures.

BACKGROUND OF THE INVENTION

It is known that physiological gas exchange and acid-base status in mature and immature humans and animals can be maintained through liquid breathing techniques ("liquid ventilation"). Due to the inherent physiological characteristics associated with liquid ventilation, it is being employed in the treatment of many different types of ailments which were heretofore difficult or impossible to treat. Examples of ailments which can now be treated in some way by liquid ventilation procedures include, without limitation, neonatal respiratory distress syndrome, adult respiratory distress syndrome, and even certain types of lung cancer.

There are many different types of liquid ventilation systems presently used by the medical profession. Examples of such conventional systems include, without limitation, pneumatic pumps systems, demand-regulated electro-mechanical bellow systems, gravity assist systems, and roller-pump systems.

As would be expected, due to frequent changes in the physiological needs of patients during liquid ventilation procedures, patients who are subjected to such procedures are monitored to determine whether there is a need to make adjustments. However, since it is labor and cost intensive to continuously monitor such patients, their status is typically monitored periodically.

Since the need for making adjustments often occurs between the periodic status checks, the patients are frequently subjected to less than optimal ventilation conditions. Depending upon the setting which needs to be adjusted, and upon the time period overwhich the patient is subjected to the less than optimal ventilation condition(s), the resulting consequences can be catastrophic.

Although medical practitioners appreciate the ways in which liquid ventilation procedures can aid them in the treatment of patients, they are hesitant of subjecting patients thereto since there is little known as to how such procedures can be safely implemented. For example, practitioners are aware that, if not properly implemented, a patient being liquid ventilated can experience any of the following conditions within a few breathing cycles: overdistention of the lungs, air way collapse, incomplete diffusion of gases to and from the patient, and the like. Moreover, if these conditions are permitted to continue for a few minutes, the patient can experience brain damage, suffocation, stroke, blindness, and even death.

Notwithstanding the possible complications which can result when subjecting patients to liquid ventilation procedures, medical practitioners are still attempting to implement these procedures in more and more clinical applications due to the advantages associated therewith. Accordingly, there is presently an immediate need for a means for safely implementing liquid ventilation procedures. To date, amidst all of today's sophisticated technology and the tens of thousands of highly skilled professionals, no such means exists. Rather, the possibility of complications materializing during a conventional liquid ventilation procedure rests largely upon the skill and knowledge of the specific practitioner implementing the procedure and the physiological strength and stability of the patient.

Definitions

The terms "pulmonary pathways" and "pulmonary system" are used herein interchangeably and refer to areas which are normally occupied by air during normal breathing cycles. Such areas include, without limitation, pulmonary channels, spaces or volumes in the trachea, left and right bronchi, bronchioles, and alveoli of the lungs.

The terms "breathing liquid" and "breathable liquid" are used herein interchangeably and refer to a liquid which has the ability to deliver oxygen into, and to remove carbon dioxide from, the pulmonary system of a patient. Examples of breathable liquids often employed in liquid ventilation procedures include, without limitation, saline, perfluorochemicals, and the like. One of the presently preferred breathing liquids are perfluorocarbon ("PFC") liquids.

For example, at or around normal human body temperatures, most types of PFC liquids are relatively inert, non-biotransformable, non-toxic and chemically and thermally stable. Moreover, these liquids are especially suited for use in liquid ventilation procedures due to their physiological characteristics such as: low surface tension (i.e., about 75% less than that of $H_2O$); high solubility for oxygen (i.e., about 16 times greater than that of saline); high solubility for carbon dioxide (i.e., about 3 times greater than that of saline); and, relative biological inertness.

The terms "liquid lavage", "liquid ventilation" and/or "liquid lavage/ventilation" are used herein interchangeably and refer to the gravity-assisted and/or the mechanically-assisted passing of a breathing liquid through at least a portion of a patient's pulmonary pathways.

SUMMARY OF THE INVENTION

One object of this invention is to provide a novel method for safely implementing liquid ventilation procedures.

Another object of this invention is to provide a self-monitored and self-adjusting liquid ventilation system.

Yet another object of this invention is to employ the novel method for safely implementing liquid ventilation procedures as a means for introducing biological agents, tracer gases, tracer liquids and/or any combination thereof into a patient via the patient's pulmonary pathways.

Even another embodiment of this invention is to provide a novel means for guiding, monitoring and regulating a patient's internal and external body temperature during liquid ventilation.

These and other objects of the present invention are provided by the advent of novel methods for introducing breathable liquids into the pulmonary system of a patient.

In accordance with one embodiment of this invention, a novel process is provided for guiding, monitoring and regulating a ventilation procedure wherein a breathing liquid is passed through at least a portion of a patient's pulmonary pathways. In this embodiment, desired ranges for certain process parameters associated with the particular ventilation system are established. Initial settings for the ventilation system are then set such that the actual conditions during the ventilation procedure fall within the established ranges (i.e., the patient's "ventilatory profile" is set). Thereafter, the ventilation procedure is commenced.

During the ventilation procedure, actual conditions are monitored. These monitored conditions relate to the aforementioned established ranges.

After monitoring the actually-occurring conditions, the novel process determines whether the initial settings need to be adjusted. If such a need exists, the adjustments can be performed by an operator after receiving appropriate signals generated by this novel process and/or by a servo-control network linked thereto.

In accordance with another embodiment of this invention, a process is provided for delivering biological agents (e.g., medicaments, tracer gases and/or liquids, etc.) into a patient through the patient's pulmonary pathways. In this embodiment, biological agents are mixed with, and/or injected into, the breathable liquid. This agent-containing liquid is then employed as the breathing medium in a liquid ventilation procedure which is guided, monitored and regulated by the novel process disclosed above.

In accordance with yet another embodiment of this invention, a process is provided for controlling a patient's internal and external body temperatures. In this embodiment, a patient's body temperature is controlled by regulating the temperature of the breathable liquids in either of the embodiments disclosed above.

Other objects, embodiments, aspects and features of this invention will be readily assessed by one skilled in the art after reading this specification.

BRIEF DESCRIPTION OF THE DRAWINGS

A more complete appreciation of the invention disclosed herein will be obtained as the same becomes better understood by reference to the following detailed description when considered in conjunction with the accompanying figures briefly described below.

FIG. 11 is a schematic of one embodiment of a temperature control system which can be used when practicing this invention.

DETAILED DESCRIPTION OF THE INVENTION

The present invention provides a means for introducing breathable liquids into a patient's pulmonary pathways.

Figure 1A:
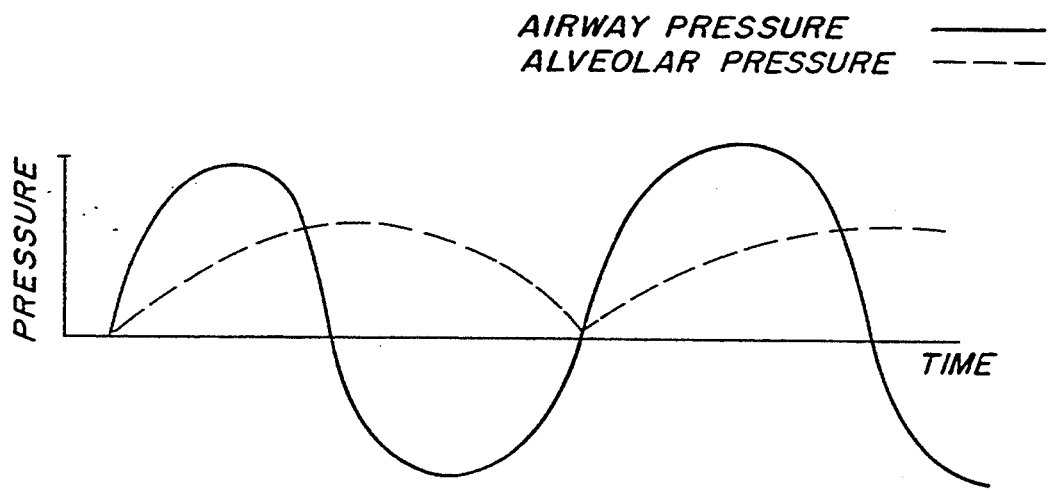
FIG. 1A, is a pressure vs. time wave form of airway pressure and alveolar pressure during a liquid ventilation procedure.
Figure 1B:
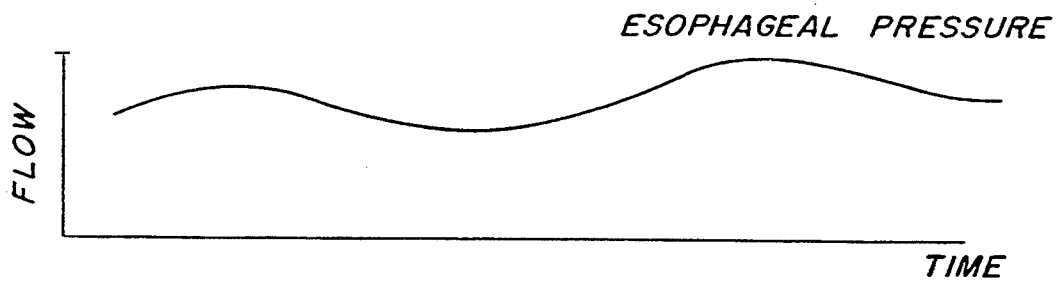
FIG. 1B, is a flow vs. time wave form of esophageal pressure during a liquid ventilation procedure.
Figure 1C:
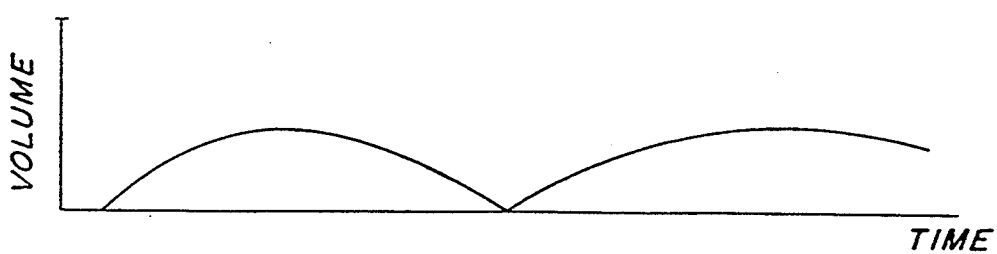
FIG. 1C, is a volume vs. time wave form showing the volume of liquid in the lung at the end of the expiratory cycle and the tidal lung liquid volume during a liquid ventilation procedure.

As shown in FIGS. 1A–C, changes in pressure, flow and volume, during a liquid ventilation procedure, follow uniform, periodic wave forms. This phenomena is significantly different from that seen in conventional gas ventilation procedures. Because of the differences in physical properties of the respiratory media (i.e., liquid vs. gas), specific wave forms for pressure, flow and volume are required for liquid ventilation procedures in order to maximize effective gas exchange, minimize cardiovascular interaction and minimize the risk of barotrauma.

Through the utilization of appropriate transducers, A/D converters and/or on-line processing devices, it is now possible to display on-line visual feedback of the liquid ventilation process as well as servo-controlled feedback information. Specifically, this information can be displayed as simultaneous pressure, flow and volume tracings as a function of time (see, FIGS. 1A-C), volume tracings as a function of pressure (see, FIG. 2), and flow tracings as the function of volume (see, FIG. 3). By mathematically manipulating this information through the use of appropriate algorithms, it is possible to establish diagnostic information on the patient as well as to determine the most effective ventilation schema (i.e., "ventilation profile").

This displayed information can be used to assess the mechanical properties of the lungs (e.g., compliance, resistance, work of breathing, pressure requirements, etc.) as well as to verify the pulmonary system's ventilatory parameters (e.g., tidal volume, minute ventilation, respiratory rate and phase, etc.). Specifically, with respect to lung mechanics, the measurement of lung compliance during liquid ventilation is unique in the diagnostic assessment of lung tissue properties independent of surface properties. On-line visual display of pressure, flow and volume relationships enables the operator to visually verify initial ventilatory patterns and establish base line conditions. An example of this is illustrated in FIGS. 2 and 3.

Figure 3:
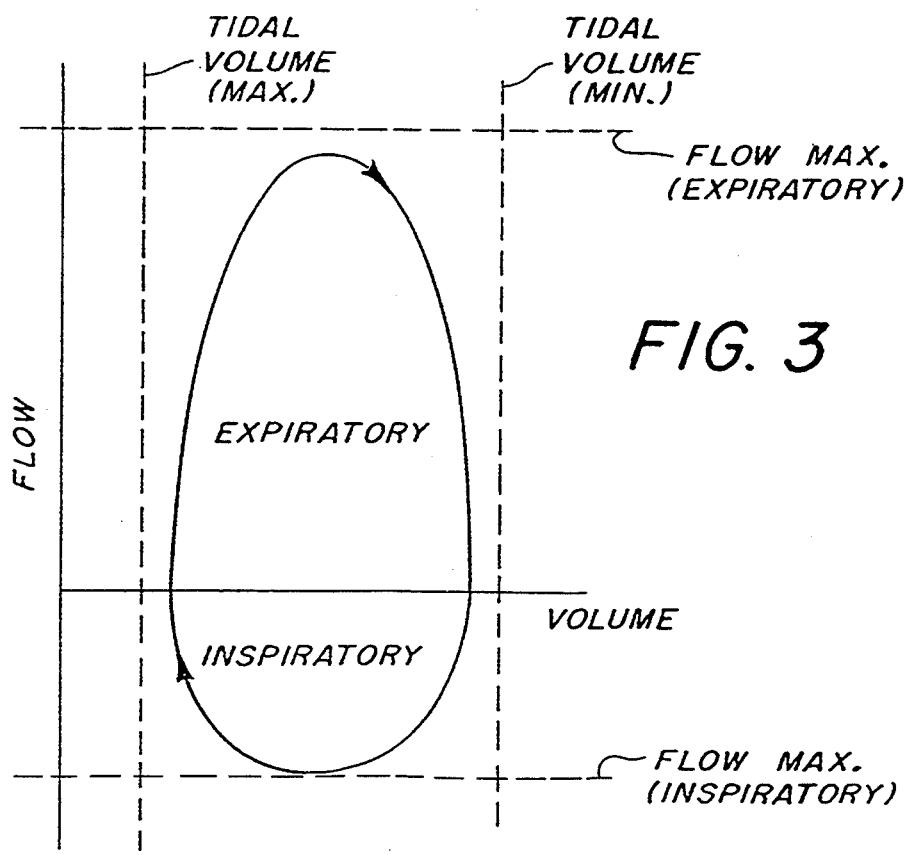
FIG. 3, is a flow vs. volume loop illustrating ideal flow and volume conditions during a liquid ventilation procedure.

For example, in FIG. 3, pressure and volume loops are controlled such that peak airway pressures, alveolar pressures and volumes are limited during inspiration and expiration. In this instance, airway pressures can be automatically regulated by feedback control of by-pass valves or through the control of driving pressures.

Alveolar pressure is determined either mathematically by on-line analysis of pressure, flow and volume or experimentally by flow interpretation. The determined alveolar pressure is then preferably regulated and limited by a microprocessor-linked control and/or by manual adjustments in liquid flow, respiratory rate and/or breathing phase. In addition, lung volume is regulated by on-line differential adjustments in inspiratory and expiratory flow (see, for example, FIG. 3).

Figure 2:
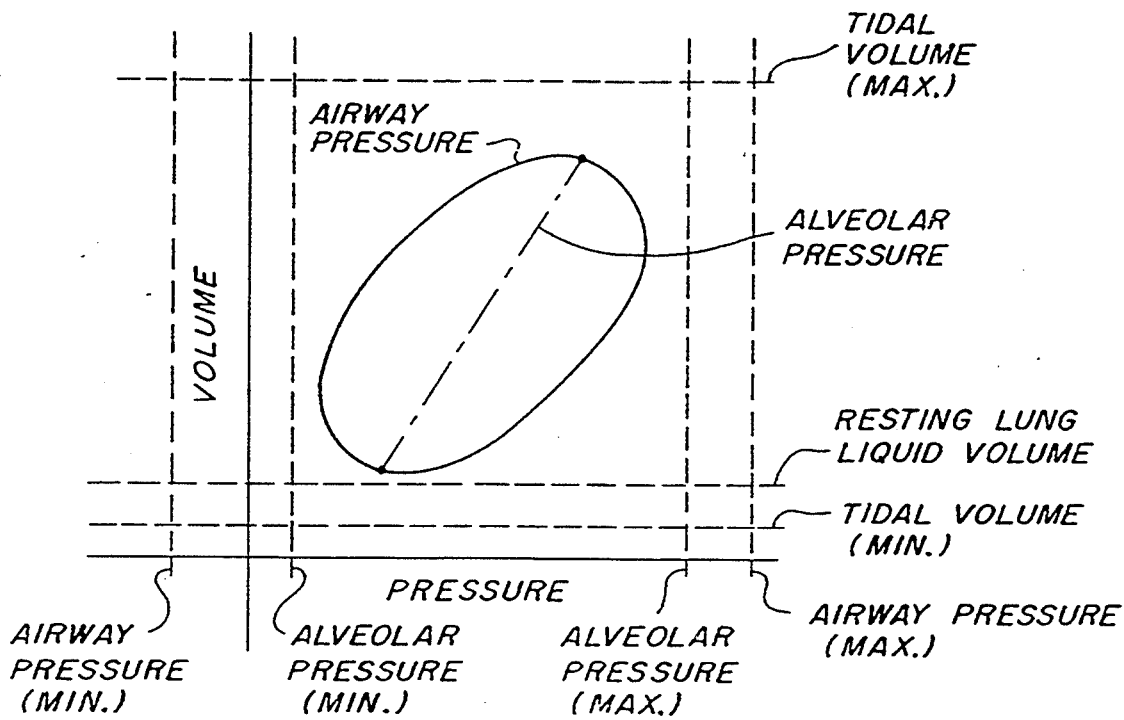
FIG. 2, is a volume vs. pressure loop illustrating ideal Volume and pressure conditions during a liquid ventilation procedure.

By employing a visual feedback such as that illustrated in FIGS. 2 and 3, it is possible to make diagnostic decisions concerning ventilation. Specifically, it is possible to detect conditions such as overdistention of the lung, airway collapse during expiration, excessive inspiratory or expiratory flow or breathing rate conditions and/or endotracheal leak or filling problems.

Figure 4:
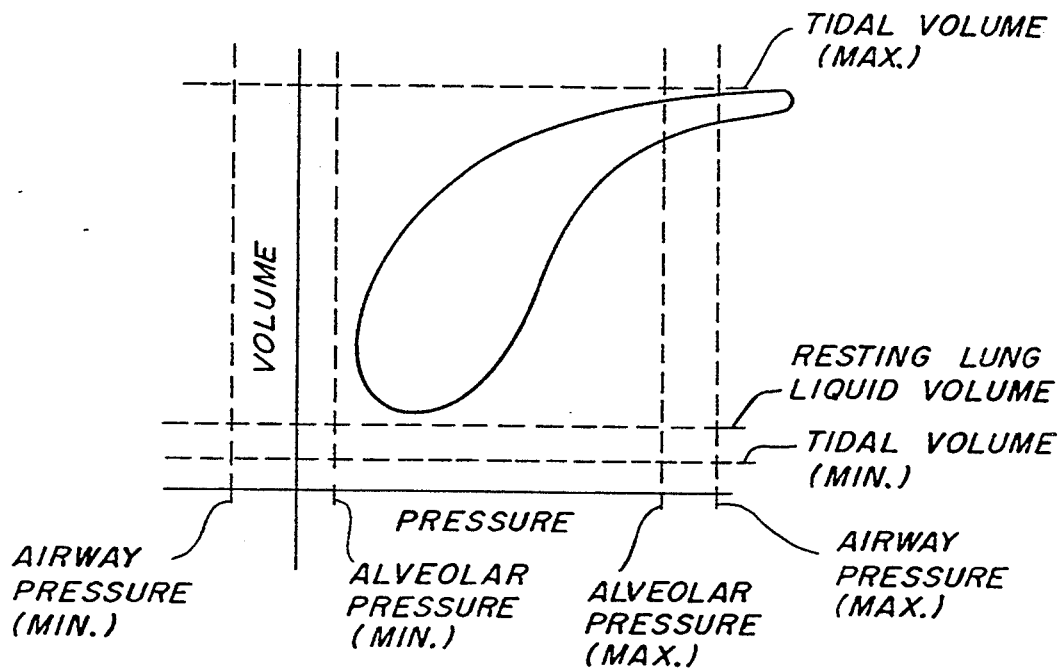
FIG. 4, is a volume vs. pressure loop illustrating overdistention pressure.
Figure 5A:
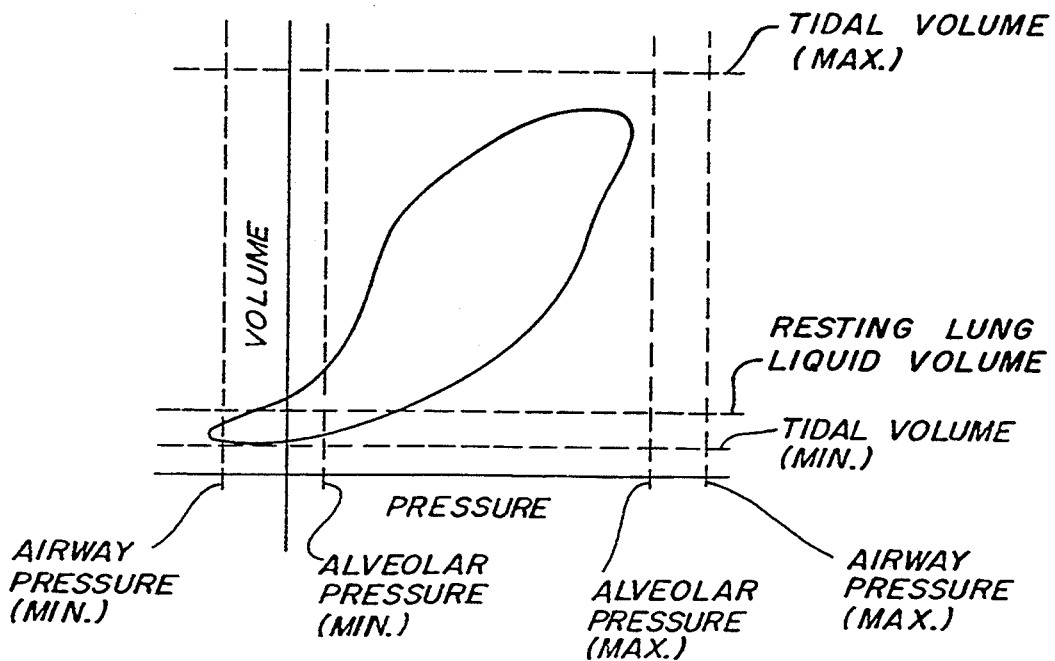
FIG. 5A, is a volume vs. pressure loop illustrating airway collapse.
Figure 5B:
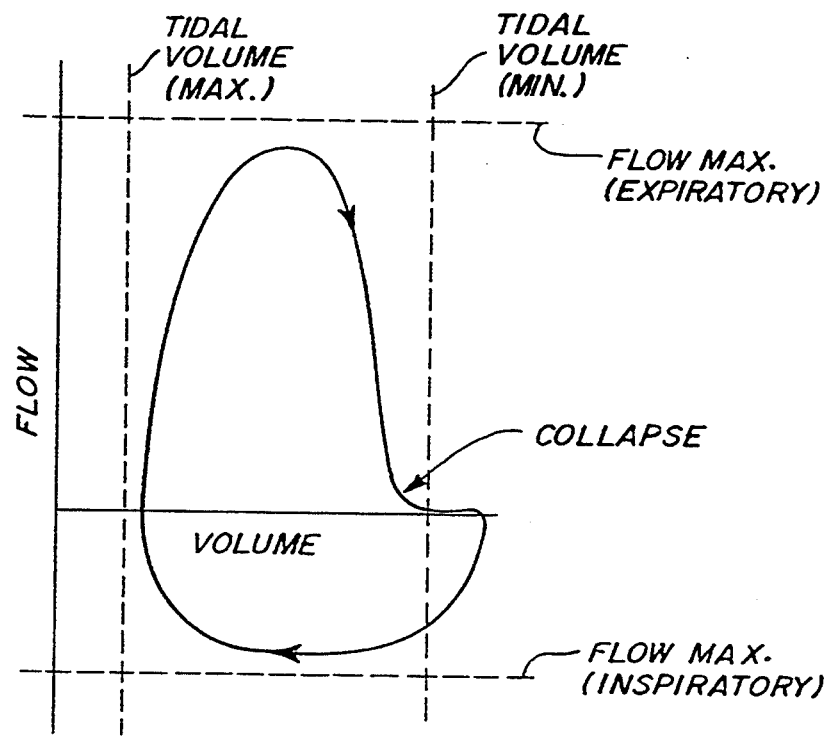
FIG. 5B, is a flow vs. volume loop illustrating airway collapse.
Figure 6:
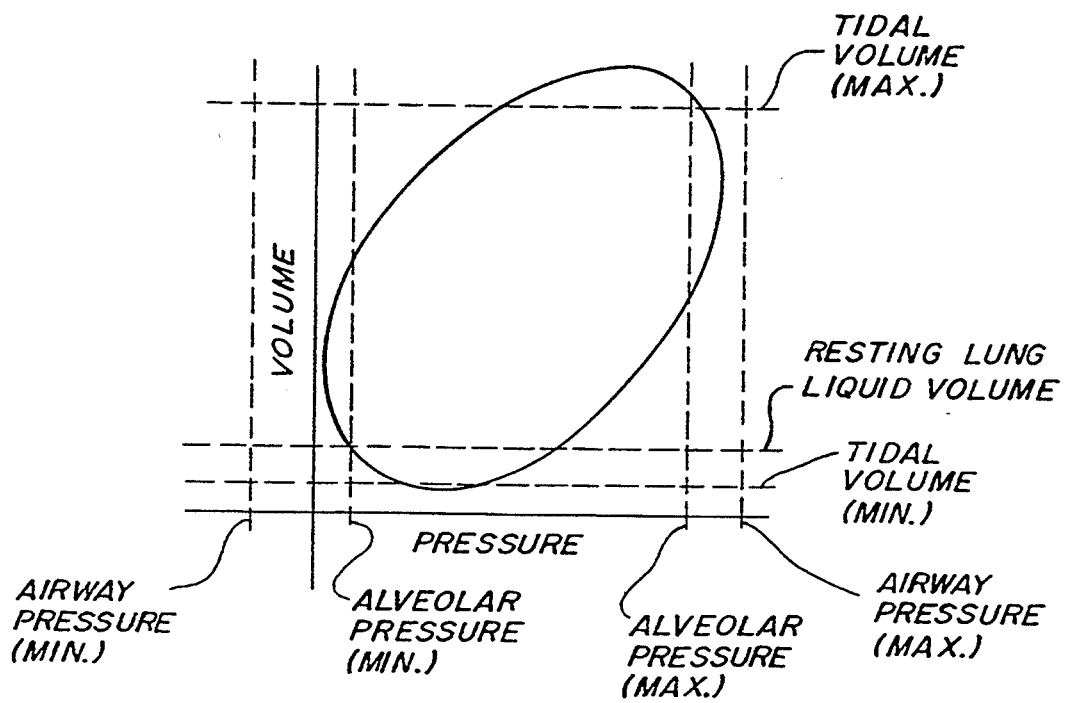
FIG. 6, is a volume vs. pressure loop illustrating excessive liquid flow.
Figure 7:
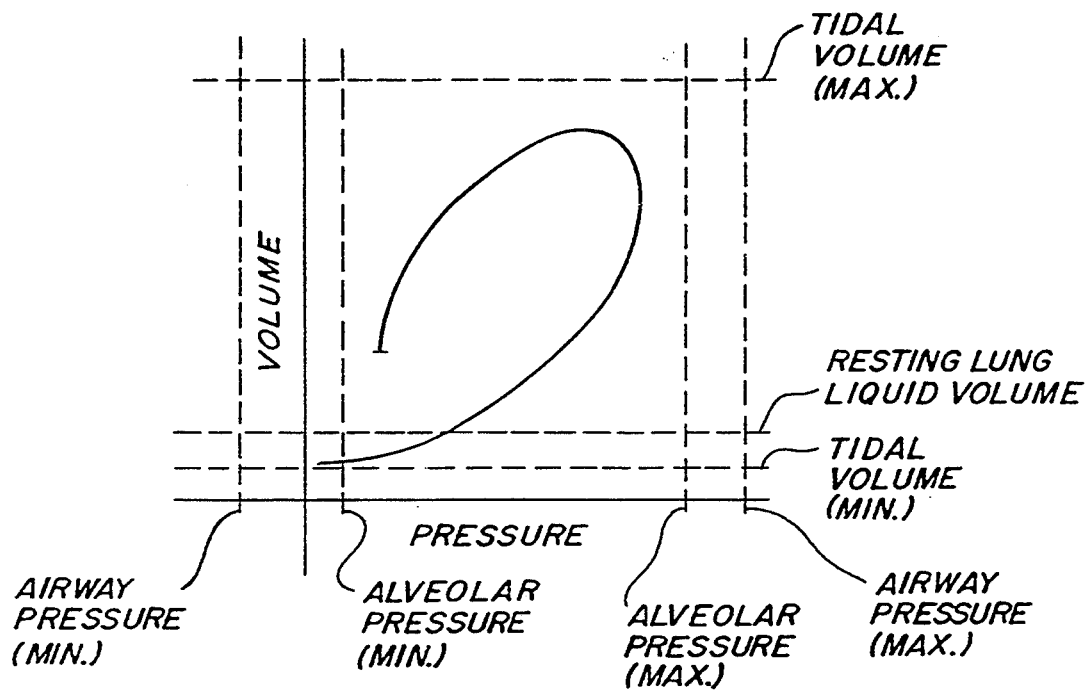
FIG. 7, is a volume vs. pressure loop illustrating a leak in the liquid ventilation system.

An example of a visual display detecting the presence of lung overdistention is illustrated in FIG. 4. Moreover, an example of a visual display detecting the presence of an airway collapse is illustrated in FIGS. 5A and 5B. In FIG. 5A, airway collapse is determined by examining volume vs. pressure. On the other hand, in FIG. 5B, airway collapse is illustrated by examining flow vs. volume. An example of a visual display indicating excessive inspiratory or expiratory flow or breathing conditions is illustrated in FIG. 6. Finally, an example of a visual display indicating an endotracheal leak is illustrated in FIG. 7.

As can be seen, by practicing this invention, it is possible to not only know whether the ventilatory parameters are within their desired ranges; but also, to know which parameters must be adjusted in order to maintain a proper liquid ventilation schema. For example, an appropriately positioned monitor can indicate that the liquid pressure is outside of its desired range. However, visual displays illustrated in FIGS. 4–7 indicate why the pressure is outside of its desired range and/or what actions need to be taken in order to rectify this problem.

It is within the purview of this invention to program a microcomputer with pressure, volume and/or flow parameters which identify liquid ventilation problems such as overdistention pressure, airway collapse, excessive flow and/or leaks. In this instance, as monitored values are fed into the microcomputer during the liquid ventilation process, the microcomputer can be designed to generate a signal which indicates which, if any, parameters need to be adjusted and by what amount.

One embodiment of this invention pertains to novel methods for guiding, monitoring and regulating process parameters of liquid ventilation systems. For purposes of better understanding this embodiment of the invention, these process parameters are being grouped into one of the following control systems: (a) a liquid control system ("LCS"), (b) a gas control system ("GCS"), and (c) a temperature control system ("TCS").

Figure 8:
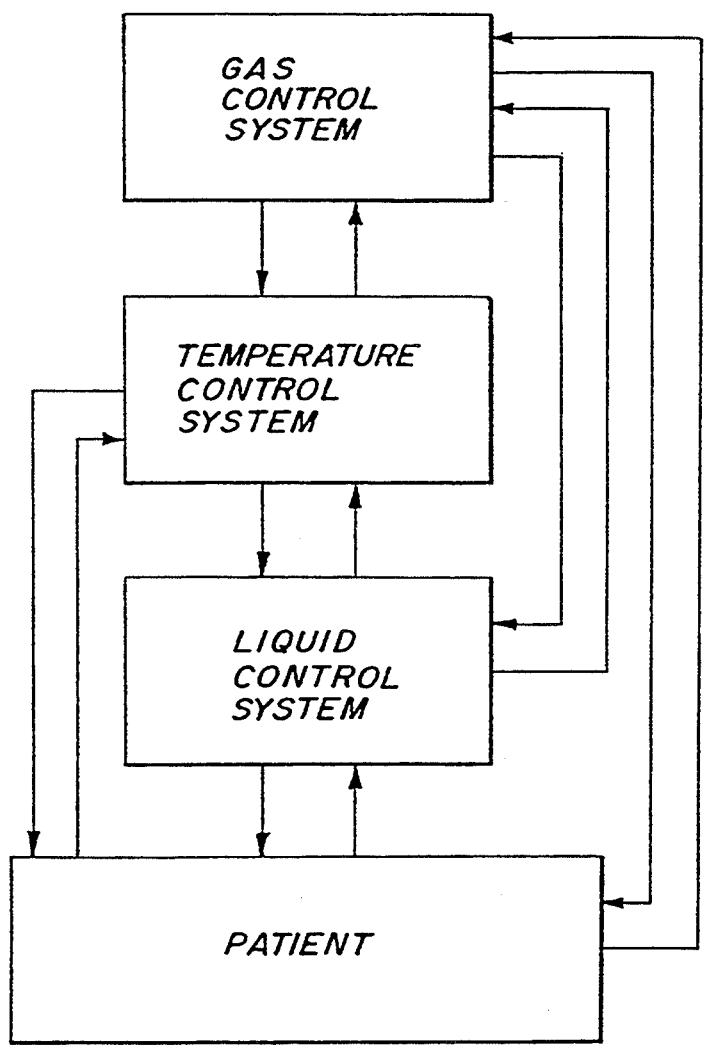
FIG. 8, is a general schematic of one embodiment of the invention illustrating the interaction between the liquid control system, the gas control system and the temperature control system with the patient being liquid ventilated.
Figure 9:
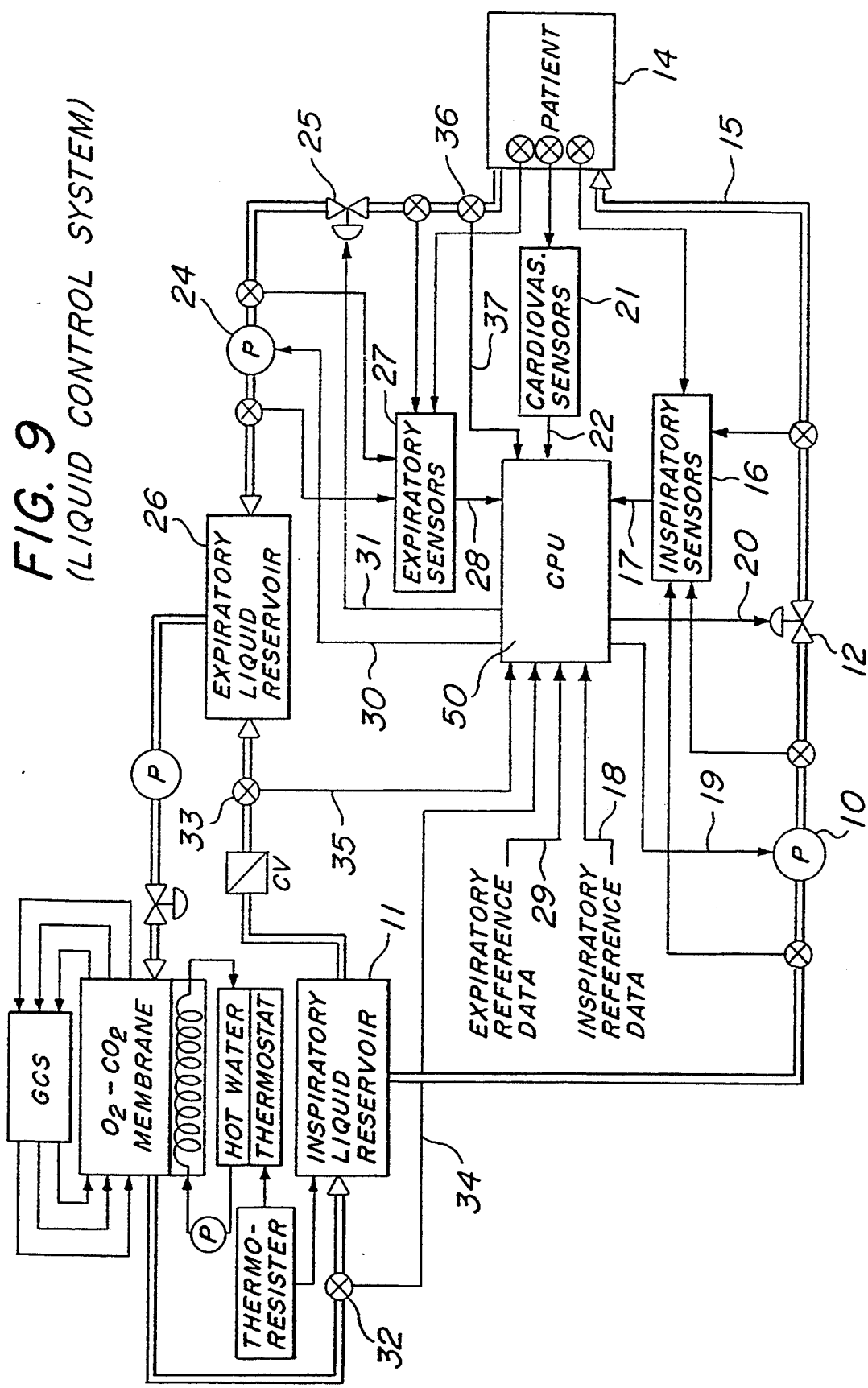
FIG. 9 is a schematic of one embodiment of a liquid control system which can be used when practicing this invention.
Figure 10:
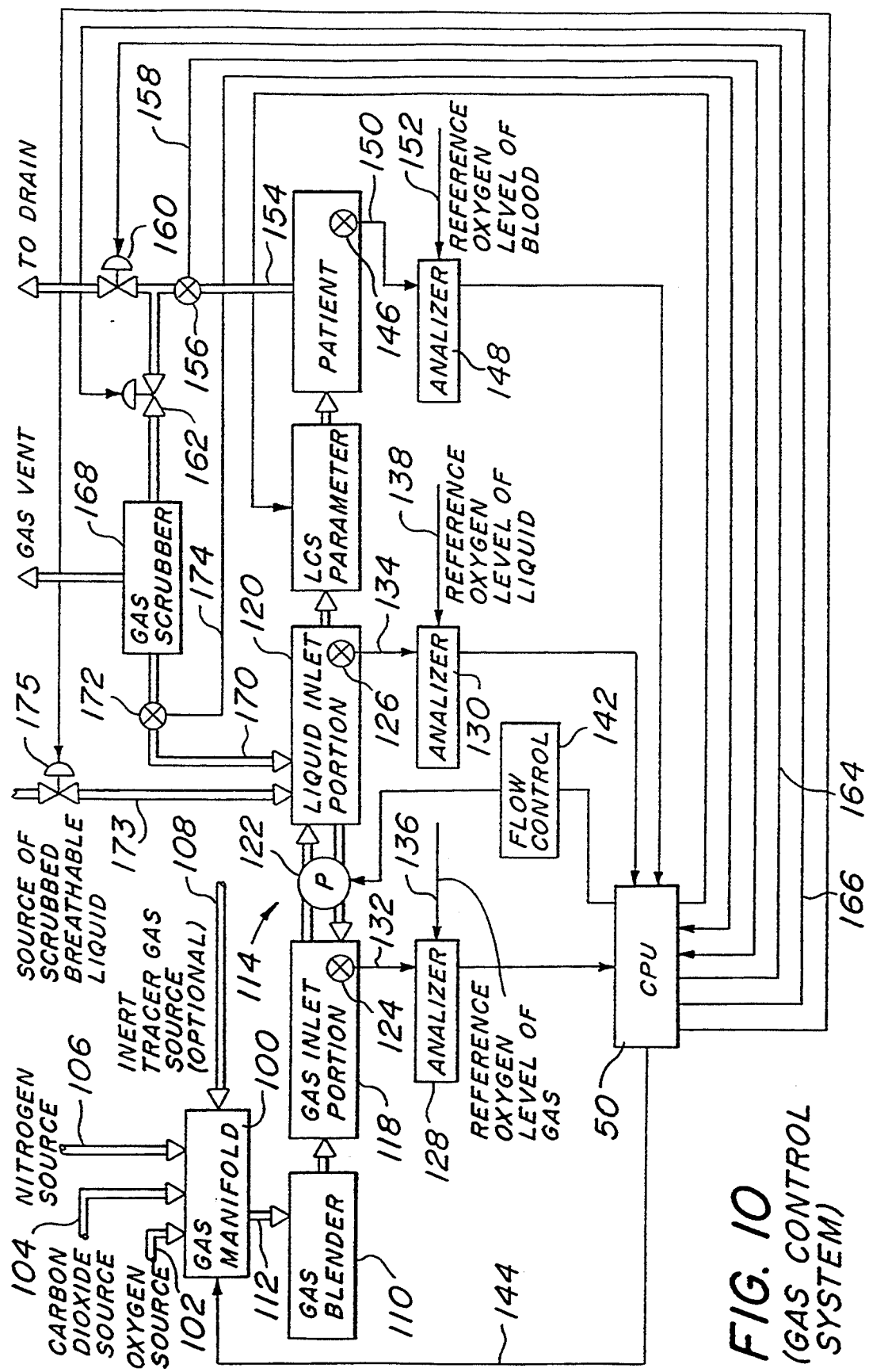
FIG. 10 is a schematic of one embodiment of a gas control system which can be used when practicing this invention.

FIG. 8 is a basic schematic of this invention's LCS, GCS and TCS, and how these control systems interact with one another and the patient. Detailed embodiments of specific LCS, GCS and TCS schematics are illustrated in FIGS. 9–11. These will be discussed later.

In general, the LCS is designed to regulate the cycling of a breathing liquid through at least a portion of a patient's pulmonary pathways during a liquid ventilation procedure. This control system utilizes information gained from an on-line assessment of the breathing liquid's pressures, flow rates and volumes. It also utilizes information gained from an assessment of the various gas levels (e.g., respiratory, tracer, etc.) contained in samples of the inspired and expired breathing liquid.

The GCS, on the other hand, is designed to guide, monitor and regulate the partial pressures, tensions and concentrations of various gases in the gas circuit, the liquid circuit and the patient. This control system utilizes information gained from an on-line assessment of inspiratory, expiratory and/or tracer gas levels (a) in the samples of the gas circuit before the gas is blended with the breathing liquid; (b) in samples of inspired and expired breathing liquid prior to inspiration and after expiration; and, (c) in blood samples taken from the patient's circulatory system during the ventilation procedure.

Moreover, the GCS can also be designed to evaluate physiological parameters which can, in turn, be used to maintain the patient's physiological stability. For example, by using inert tracer gases simultaneously with respiratory gases, it is possible to determine physiological parameters such as: oxygen consumption, carbon dioxide production, respiratory quotient, cardiac output, effective pulmonary blood flow, diffusional dead space, anatomic dead space, intrapulmonary and extrapulmonary shunts, diffusion capacity, lung tissue water, and the like.

Finally, the TCS is designed to guide, monitor and regulate the patient's internal and/or external body temperatures during a liquid ventilation procedure. This control system utilizes information gained from temperature sensing means in and/or on appropriate body parts, organs and/or regions of the patient.

For example, the TCS can be designed to guide, monitor and regulate a patient's internal body temperature by regulating the temperature of the inspired breathing liquid. On the other hand, the TCS can be designed to guide, monitor and regulate a patient's external body temperature by adjusting the surface temperature of the patient's body.

Maintaining internal and external body temperatures within established ranges is extremely important during a liquid ventilation procedure. For example, if temperatures are not carefully maintained within a few degrees of a body's thermal neutral zone, the patient may suffer physiological consequences such as thermal shock, cardiac arrest, cerebral hemorrhage, pulmonary hemorrhage, metabolic complications due to impaired gas exchange, cardiopulmonary instability and even death.

The novel control process of this invention is adaptable to most liquid ventilation systems. The preferred d ventilation system depends, in part, upon the specific needs of the patient and the resources available to the medical practitioner. Once these variables have been identified, a skilled artisan will be able to select, the most appropriate liquid ventilation system.

Each of the aforementioned process control systems (i.e., the LCS, GCS and TCS) has associated therewith a number of parameters which are designed to be guided, monitored and regulated prior to, during and/or after the liquid ventilation procedure. The specific set of parameters which are controlled during the ventilation procedure depend, in part, upon the patient's needs and the specific liquid ventilation system employed.

In accordance with this invention, prior to initiating the liquid ventilation procedure, the patient's initial ventilatory profile is established. Here, desired ranges for certain process parameters are determined depending upon the specific needs of the patient. In most instances, when establishing a patient's initial ventilatory profile, desired ranges for the following parameters are determined: (a) the breathing liquid's pressure, flow rate, tidal lung liquid volume, and resting lung liquid volume; (b) the concentration of various gases in specific volumes of the gas circuit, inspired and expired breathing liquids, and the patient's circulatory system; and, (c) the patient's internal and external body temperatures during the liquid ventilation procedure, as well as the temperature of the inspired breathing liquid.

Some of the ranges which are established for parameters associated with LCS are minimum and maximum values for the following: (a) the breathing liquid's pressure for when it is passing through the patient's pulmonary pathways; (b) the breathing liquid's tidal lung liquid volume for when it is passing through the patient's pulmonary pathways; (c) the breathing liquid's resting lung liquid volume during the liquid ventilation procedure; (d) the breathing liquid's flow rate for when it is passing through the patient's pulmonary pathways; (e) the amount of oxygen to be absorbed from a specific volume of inspired breathing liquid by the patient; and (f) the amount of carbon dioxide to be absorbed from the patient by a specific volume of expired breathing liquid.

The aforementioned list of ranges established for LCS-related parameters is not inclusive. Specifically, another range which can be established for the LCS is the minimum and maximum values for the amount of tracer gases (e.g., hydrogen, nitrogen oxide, argon, etc.), if used, to be absorbed from a specific volume of inspired breathing liquid by the patient.

For simplicity reasons, the operation of the LCS can be broken down into three sublevels of control. The first sublevel of control is designed to guide liquid pressures, liquid flow rates and liquid volumes, as well as, to guide the amount of gases absorbed from and/or by the breathing liquid before and during the ventilation procedure. Although any suitable means can be employed to achieve this objective, it is presently preferred to employ a series of variable flow and/or pressure means.

The second sublevel of control for the LCS is designed to monitor actual liquid pressures, liquid flow rates and liquid volumes, as well as, to monitor the amount of gases absorbed from and/or by the breathing liquid before and during the ventilation procedure. Although any suitable means can be employed to achieve this objective, it is presently preferred to employ a series of liquid and/or gas sensors.

The third sublevel of control for the LCS is designed to evaluate the information monitored from the LCS's second sublevel of control. This third sublevel of control can also be designed to determine whether any adjustments need to be made to the liquid ventilation procedure. Although any suitable means can be employed to achieve this objective, it is presently preferred to employ a central processing unit which is programmed to accept the initial settings, receive the monitored values and make the necessary comparisons and computations.

One example of a method in which a LCS can be designed to perform each of the aforementioned sublevels of control in accordance with the present invention is illustrated in FIG. 9. A detailed description of this embodiment will be provided later.

Regarding the GCS, some of the ranges which are established for parameters associated therewith are minimum and maximum values for the following: (a) the concentration of oxygen in a specific volume of the gas being blended with the breathing liquid; (b) the concentration of oxygen in a specific volume of the breathing liquid prior to its inspiration by the patient; (c) the concentration of oxygen in a specific volume of expired breathing liquid; (d) the concentration of carbon dioxide in a specific volume of expired breathing liquid; and, (e) the concentration of oxygen in the patient's circulatory system during the liquid ventilation procedure.

Since breathing liquid is relatively expensive, in most liquid ventilation procedures, expired breathing liquid is recycled, Under these circumstances, prior to its reuse, the breathing liquid must be scrubbed clean of undesired expiratory gases contained therein (e.g., carbon dioxide). Therefore, if the breathing liquid is to be recycled, another range which must be established for a GCS-related parameter is minimum and maximum values for the concentration of carbon dioxide in a specific volume of the breathing liquid, prior to its re-inspiration by the patient.

The aforementioned list of ranges established for GCS-related parameters is not inclusive. Specifically, another range which can be established for the GCS is the minimum and maximum values for the concentration of tracer gases (e.g., helium, argon, nitrogen oxide, etc.), if used, in a specific volume of inspired and/or expired breathing liquid.

Any suitable means can be employed to guide, monitor and regulate the concentration of gases within the gas circuit, the liquid circuit, and the patient. One of the presently-preferred configurations employs a series of gas sensors, pumps and/or valves.

For simplicity reasons, the operation of the GCS can also be broken down into three sublevels of control. The first sublevel of control for the GCS is designed to guide, monitor and regulate the concentration of various respiratory and tracer gases within the gas circuit, prior to mixing the gas(es) with the breathing liquid. In this GCS sublevel of control, the system is designed to determine, among other things, whether the gas stream has the proper concentration of oxygen therein.

The second sublevel of control for the GCS is designed to guide, monitor and regulate the concentration of various respiratory and tracer gases within the breathing liquid after the oxygen-containing gas has been mixed therewith. In this GCS sublevel of control, the system is designed to determine, among other things, whether the breathing liquid has been effectively oxygenated. This determination is made before the oxygenated breathing liquid is inspired by the patient.

The third sublevel of control for the GCS is designed to guide, monitor and regulate the concentration of various respiratory and tracer gases, if used, within the patient during the liquid ventilation procedure. In this GCS sublevel of control, the system is designed to determine, among other things, whether the desired level of oxygenation in the patient has been attained.

This third sublevel of control for the GCS is the most important of all. For example, even if the other GCS sublevels of control are operating within their desired parameters, if the patient is not receiving a sufficient amount of oxygen, some adjustments must be made.

There are many ways of controlling the level of oxygenation within a patient in accordance with the present invention. For example, with regard to the GCS's first sublevel of control, adjustments can be made which are designed to alter the concentration of oxygen within the gas circuit. Moreover, with regard to the GCS's second sublevel of control, adjustments can be made which are designed to alter the concentration of oxygen in the breathing liquid prior to its inspiration by the patient. Either of these procedures, when performed individually or collectively, can alter the patient's oxygenation level.

In addition to the above, the level of oxygenation within a patient can be adjusted in accordance with the present invention by making certain alterations to the LCS's parameters. Specifically, by altering the flow rate of the oxygenated breathing liquid through the patient's pulmonary system and/or by altering the resting lung liquid volume or the tidal lung liquid volume, the patient's level of oxygenation can also be altered.

The specific parameter(s) of the various control system(s) which need(s) to be adjusted will be determined, at least in part, by the specific volume vs. pressure loop and the specific flow vs. volume loop (see, for example, FIGS. 2 and 3) associated with the patient's ventilatory profile. In other words, after the control system(s) of the present invention indicate(s) that at least one of the parameters is outside of its desired range, the aforementioned loops are evaluated to determine which parameter(s) need(s) to be adjusted in order to rectify the problem and by what amount.

One example of a method in which a GCS can be designed to perform each of the aforementioned sublevels of control in accordance with the present invention is illustrated in FIG. 10. A detailed description of this embodiment will be provided later.

Regarding the TCS, some of the ranges which are established for parameters associated therewith are minimum and maximum values for the following: (a) the temperature of the inspired breathing liquid prior to its inspiration by the patient; (b) the patient's internal body temperature during the liquid ventilation procedure; and (c) the patient's external body temperature during the liquid ventilation procedure.

The aforementioned list Of ranges established for TCS-related parameters is not inclusive. Specifically, other ranges which can be established for the TCS include, without limitation, the minimum and maximum values for the temperature of the gases within the gas circuit and/or the breathing liquid prior to the two being mixed together; the temperature of the breathing liquid as it is passing through the patient's pulmonary pathways; and, the temperature of the expired breathing liquid.

Any suitable means known to those skilled in the art can be employed to guide, monitor and regulate patient's internal and external body temperatures, as well as the temperatures of the gas and liquid circuits. One presently-preferred configuration employs a series thermal sensors, heating/cooling sources, pumps and blending valves.

In this preferred embodiment, temperature regulation of the body, or a region thereof, can be accomplished by internal and/or external means. For example, a patient's internal body temperature can be manipulated by a heating/cooling means which is designed to regulate the temperature of the inspired breathing liquid. On the other hand, a patient's external body temperature can be manipulated by a heating/cooling means which is designed to regulate the temperature of the patient's body surface.

One example of a method in which a TCS can be designed to perform in accordance with the present invention is illustrated in FIG. 11. A detailed description of this embodiment will be provided later.

When establishing the desired parameters associated with the LCS, GCS and TCS in accordance with the present invention, it is necessary to take at least the following into consideration: the specific liquid ventilation system employed, the patient's specific physiological conditions, and the purpose for which the patient is being liquid ventilated. Once the patient has been identified and the appropriate considerations have been made, a skilled artisan can readily establish the desired parameter ranges.

The optimum desired ranges of the LCS's and TCS's parameters vary greatly among patients. However, the degree of variance is not as great when dealing with the optimum desired ranges of the GCS's parameters for adult humans. For example, for most adult human patients without lung disease, the desired oxygen concentration in the inspired breathing liquid generally ranges from between about 300 to about 400 mmHg. On the other hand, for most adult human patients with lung disease, the desired oxygen concentration in the inspired breathing liquid generally ranges from between about 400 to about 600 mmHg.

Moreover, for most adult human patients, the desired oxygenation levels in the patient's circulatory system are as follows: an oxygen tension generally ranging from between about 80 to about 100 mmHg, and an arterial oxygen saturation point generally greater than about 85%.

After the desired ranges of parameters associated with the LCS, the GCS and the TCS are established in accordance with the present invention, settings for patient's initial ventilatory profile are set. These initial settings are adjusted accordingly so that the actual conditions which will be monitored or calculated during the liquid ventilation procedure fall within the established desired ranges.

The adjustment of these initial settings depend, in part, upon the specific liquid ventilation system employed and the specific needs of the patient. However, regardless of these specifics, the following initial settings must be made: (a) the starting lung liquid volume, (b) the breathing liquid's initial pressure, (c) the initial tidal lung liquid volume, (d) the breathing liquid's initial flow rate, (e) the initial concentration of oxygen in a specific volume of the breathing liquid prior to its inspiration by the patient, (f) the resting lung liquid volume, (g) the peak inspiratory and expiratory air way pressures, (h) the peak alveolar and esophageal pressures, (i) the breathing frequency, (j) the timing ratio of inspiratory-to-expiratory liquid flow, (k) the patient's core body temperature, and (l) the temperature of the breathing liquid prior to it being inspired by the patient.

The aforementioned list of initial settings is not inclusive. Specifically, as stated earlier, expired breathing liquid is generally recycled. Therefore, in most instances, the expired breathing liquid must be scrubbed clean from all unnecessary gases such as carbon dioxide. Accordingly, under these circumstances, another initial setting which must be made is the concentration of carbon dioxide in a specific volume of the breathing liquid, prior to its re-inspiration by the patient.

The optimum initial ventilatory profile differs among patients. However, for many normal adult humans, the typical initial settings are adjusted to fall within the following ranges: (a) a starting lung liquid volume ranging from between about 20 to about 30 ml/kg, (b) the breathing liquid's initial pressure ranging from between about −50 to about 50 cmH$_2$O, (c) the tidal lung liquid volume ranging from between about 10 to about 20 ml/kg, (d) the breathing liquids initial flow rate ranging from between about −300 to about 300 ml/mm/kg, (e) the initial concentration of oxygen in a specific volume of breathing liquid ranging from between about 100 to about 600 mmHg, (f) the patient's resting lung liquid volume ranging from between about 20 to about 40 ml/kg, (g) the peak inspiratory and expiratory airway pressures ranging from between about 80 to about 100 cmH$_2$O, and from between about −80 to about −100 cmH$_2$O, respectively, (h) the peak alveolar and esophageal pressures ranging from between about 15 to about 20 cmH$_2$O, and from between about 15 to about 20 cmH$_2$O, respectively, (i) the breathing frequency ranging from between about 3 to about 8 breaths per minute, (j) the timing ratio of inspiratory-to-expiratory gas ranging from between about 1:2 to about 1:4, (k) the patient's core body temperature ranging from between about 25° to about 39° C., and (l) the breathing liquid's temperature, prior to inspiration, ranging from between about 20° to about 42° C.

Once the initial settings of the LCS's, GCS's, and TCS's parameters are set this information is fed into a central processing unit. Thereafter, the liquid ventilation procedure is commenced.

As stated earlier, in accordance with this invention, while the patient is being liquid ventilated, certain actual conditions are monitored. The monitored conditions relate to the aforementioned established desired ranges and the patient's initial ventilatory profile.

Any suitable method can be employed to monitor the patient's and the control systems' physiological parameters during the liquid ventilation procedure being practiced in accordance with the present invention. Examples of some of the more preferred monitoring methods include, without limitation the implementation of sensors, transducers, A/D converters, on-line processing units and/or the like.

After the actual liquid ventilation conditions have been monitored and/or calculated, they are evaluated by being compared to their respective desired ranges as established prior to the commencement of the liquid ventilation procedure. This comparison provides information which is necessary to maintain the patient's optimum ventilatory profile.

For example, if the liquid, gas, patient loop is considered a closed system, then the amount of oxygen added to the gas system equals the amount absorbed by the liquid system. The amount consumed by the patient equals this amount less the amount of oxygen present in the expired breathing liquid. Therefore, by monitoring the oxygen concentration levels present in the closed system and by regulating the amount of oxygen added thereto, the oxygen consumption by the patient can be evaluated and controlled.

Moreover, expired breathing liquid is sampled in order to monitor the oxygen and carbon dioxide concentrations therein. In addition, the oxygen concentration in the patient's blood is also monitored. With this information, the optimum respiratory rate and tidal lung liquid volume needed for maximizing carbon dioxide elimination from, and oxygen delivery to the patient can be determined.

In accordance with this invention, the monitored conditions can be evaluated by any suitable means known to those skilled in the art. As stated above, one of the preferred methods for making such evaluations employs the use of an on-line central processing unit ("CPU"). Here, the established desired ranges, the initial ventilatory profile and the actual monitored conditions are into the CPU. The CPU then makes the necessary comparisons and/or computations.

evaluation indicates that the monitored parameters are not being maintained within their desired ranges, the CPU will generate a signal which is designed to sound an alarm and/or to activate a servo-controlled valving network. This generated signal will be based, at least in part, on the patient's optimum volume vs. pressure loop and/or the patient's optimum flow vs. volume loop.

The CPU can be used to control the breathing liquid's pressure and volume loops such that peak airway pressures, alveolar pressures and volumes will be limited during inspiration and expiration. Under such conditions, a CPU-linked servo-control network can be used to automatically regulate airway pressures by feedback control of by-pass valves and/or by control of driving pressures. The CPU can also be used to determine alveolar pressure by an on-line analysis of pressure, flow and volume data as supplied thereto by appropriately positioned sensors.

The CPU is also preferably used to guide, monitor and regulate the oxygen concentration levels within the patient. In this preferred embodiment, the CPU continuously monitors the oxygen concentration levels within the gas circuit, the liquid circuit and the patient. If the level of oxygen within the patient is outside of the desired range, the CPU can generate a signal which is designed to make the necessary adjustments.

For example, the oxygen concentration can be adjusted by a CPU-linked servo-control network which regulates the oxygen concentration in the gas-liquid exchanger. This would change the oxygen concentration in a specific volume of inspired breathing liquid. Also, the CPU-linked servo-control network can regulate the flow rate of breathing liquid through gas-liquid exchanger. This would also effect the oxygen concentration in a specific volume of inspired breathing liquid.

The CPU can even generate signals which are designed to activate alarms and/or produce messages which instruct an operator to make the necessary adjustments. Although this latter method is not as automated as the others, it may still be the most preferred technique depending upon the specific needs of the patient.

The CPU can also generate signals which are designed to adjust oxygen concentration levels by regulating the LCS. Specifically, adjusting the rate at which the breathing liquid passes through the patient's pulmonary pathway affects the amount of oxygen absorbed by the patient.

Therefore, a CPU can generate signals which are designed to adjust both the oxygen concentration level within the inspired breathing liquid and the rate at which the oxygenated liquid flows through the patients lungs. Since the CPU can be programmed to instantaneously determine the optimum ventilatory profile for the specific patient, the amount of time that a patient is subjected to the less than optimal conditions is substantially decreased.

As with the aforementioned control systems, it is presently preferred to employ a CPU to guide, monitor and regulate the patient's internal and/or external body temperature during the liquid ventilation procedure and the temperature of the breathing liquid prior to it being inspired by the patient. In this preferred embodiment, the desired temperatures can be maintained by the CPU regulating the temperature of the breathing liquid, and/or by regulating the temperature of the patient's extremities, trunk and head.

As stated earlier, thermal sensors are preferably used to monitor the patient's internal and external body temperatures. The positioning of sensors depends, in part, on the temperature being monitored.

Although the optimum positioning of sensors depends upon the specifics surrounding the particular patient and liquid ventilation system being employed, in many instances, one internal body temperature sensor is typically placed adjacent to the lung. Moreover, external body temperature sensors are typically placed in or on the following locations: (a) in the esophagus and rectum in order to monitor the core temperature of the patient's trunk, (b) adjacent to the tympanic membrane in order to monitor core temperatures of the patient's head, (c) on each of the extremities in order to monitor the patient's surface peripheral body temperature, (d) in the heating and/or cooling sources in order to monitor their respective temperatures, (e) in the inspired gas flow circuit, and (f) in the condenser circuit for the expired gas flow.

In accordance with this invention, heating and/or cooling means are used to directly or indirectly regulate the internal and external body temperatures. Such heating and/or cooling means can be used to regulate the temperature of the inspired gas and liquid, the extremities, the trunk and/or the head. Moreover, such heating and/or cooling means can be in the form of convective hot/cold fluid in individually controlled surface blankets, convective hot/cold gas on the body surface, radiant generated heat, microwave generated heat and/or radiation heat sources and heat exchangers within the liquid and/or gas circuits.

Figure 12A:
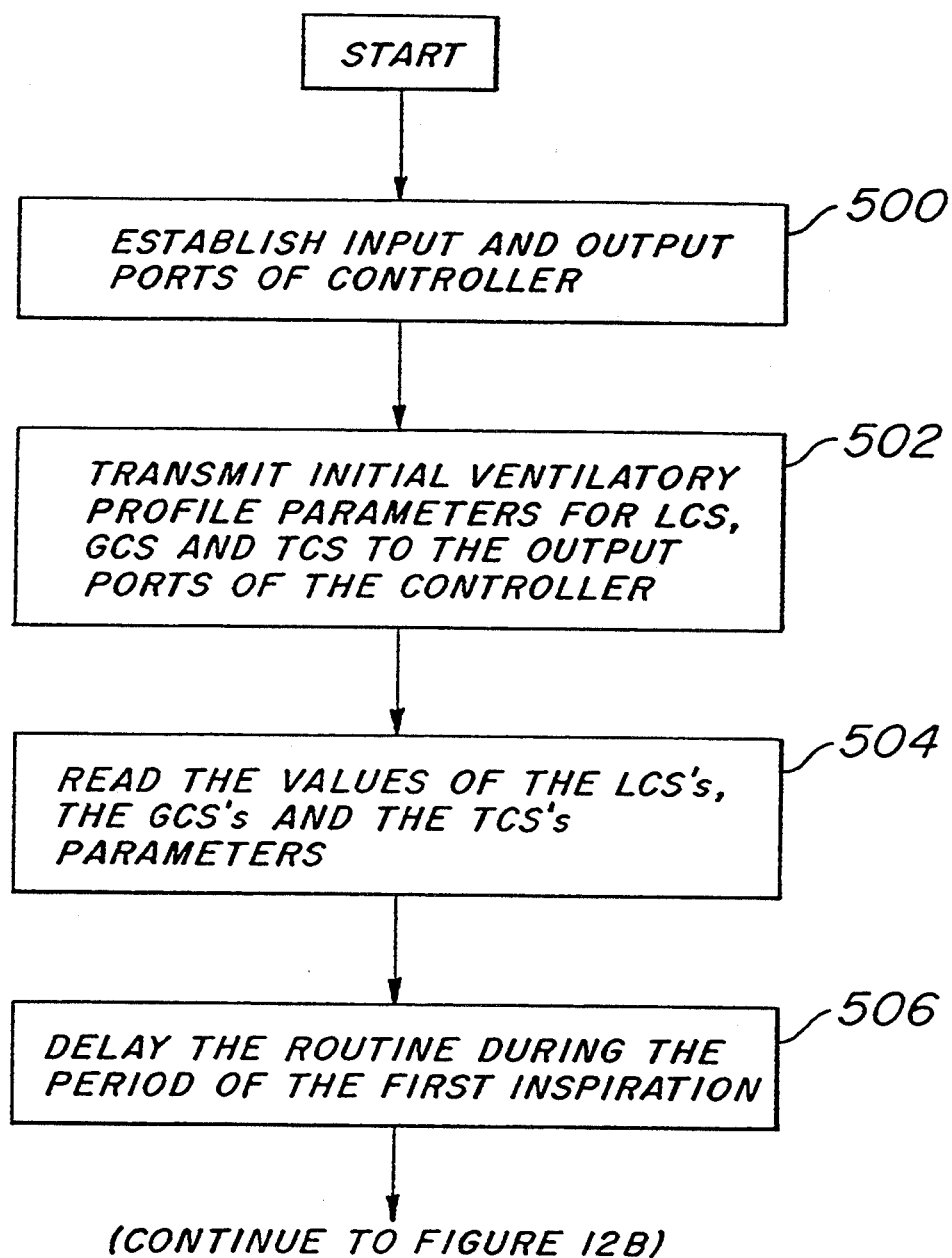
FIGS. 12A–12C are a flow chart illustrating a preferred sequence of steps executed by the programmable controller for carrying out the method of the present invention.
Figure 12B:
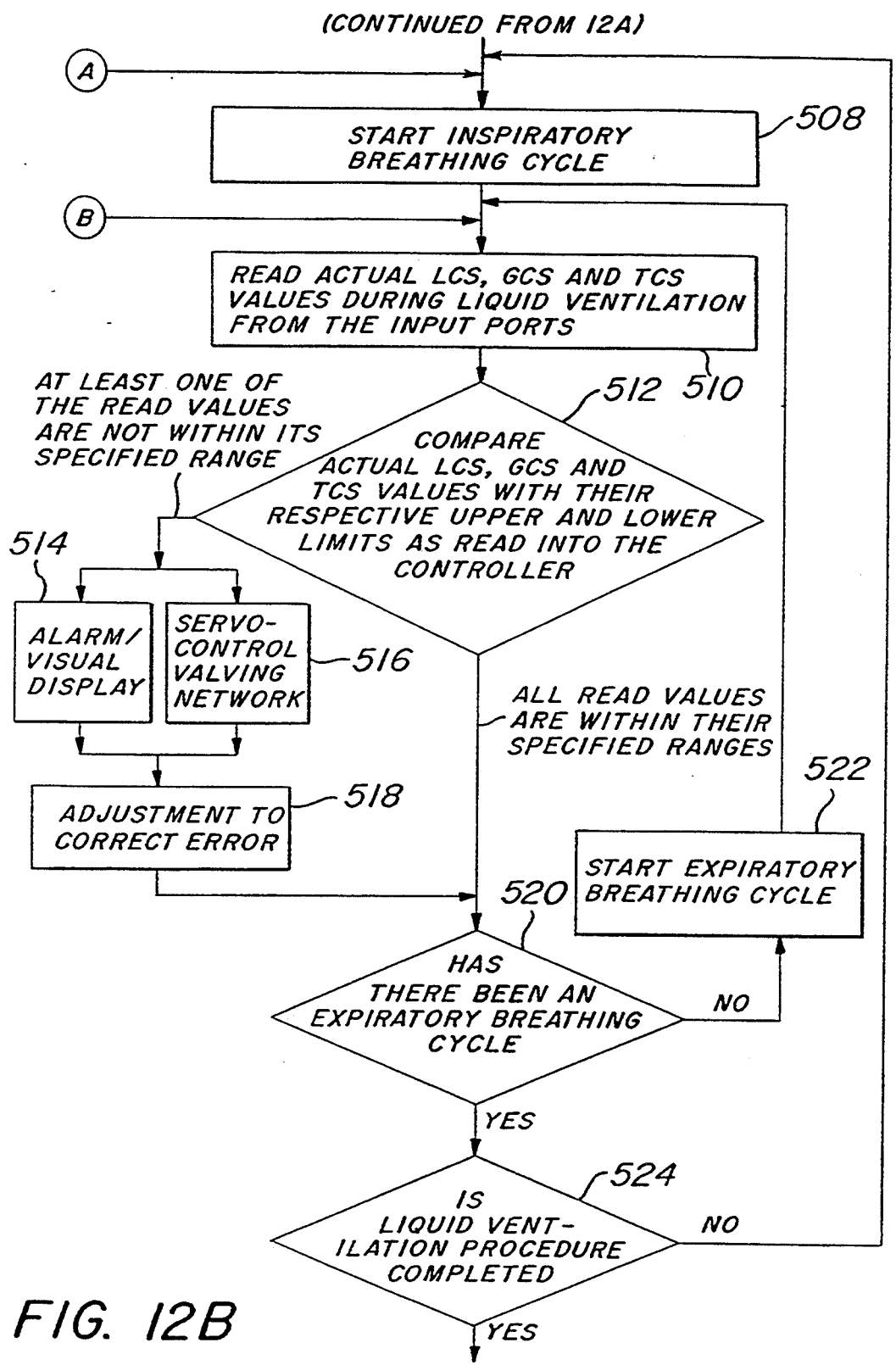

Referring to FIGS. 12A–12B, there is illustrated flow chart of the sequence of steps to be performed by a central processing unit in a preferred practice of the method of the present invention. Those skilled in the art will appreciate that the illustrated sequence of steps may be easily reduced to source code instructions which can be input into and/or executed by a digital processor.

At the start of the flow chart, desired ranges for the various control system's parameters are established at 500. Moreover, patient cardiovascular and blood gas parameters are also established at 500. These parameters are then transmitted to the output ports of the central processing unit as shown in 502.

Values representing parameters associated with the patient's initial ventilatory file are then fed into the central processing unit, or retrieved from its memory if stored, as shown in 504.

The types of values associated with the LCS which are read include: (a) the breathing liquid's pressure for when it is passing through the patient's pulmonary pathways; (b) the breathing liquid's tidal lung liquid volume for when it is passing through the patient's pulmonary pathways; (c) the breathing liquid's resting lung liquid volume during the liquid ventilation procedure; (d) the breathing liquid's flow rate when it is passing through the patient's pulmonary pathways; (e) the amount of oxygen absorbed from the specific volume of inspired breathing liquid by the patient; and, (f) the amount of carbon dioxide absorbed from the patient by a specific volume of breathing liquid.

The types of values associated with the GCS which are read include: (a) the concentration of oxygen in a specific volume of the gas being blended with the breathing liquid; (b) the concentration of oxygen in a specific volume of the breathing liquid prior to its inspiration by the patient; (c) the concentration of oxygen in a specific volume of expired breathing liquid; (d) the concentration of carbon dioxide in a specific volume of expired breathing liquid; and, (e) the concentration of oxygen in the patient's circulatory system during the liquid ventilation procedure.

The type of values associated with the TCS which are read include: (a) the temperature of the inspired breathing liquid prior to its inspiration by the patient; (b) the patient's internal body temperature during the liquid ventilation procedure; and, (c) the patient's internal body temperature during the liquid ventilation procedure.

At step 506, the program routine is delayed during the period of the first inspiration.

In this preferred embodiment, sensors are provided for the continuous measurement of the aforementioned LCS, GCS and TCS inspiratory- and expiratory-related values. Specifically, the central processing unit reads continuously monitored inspiratory-related data via its input ports during the execution of the ventilatory loop illustrated at "A". Similarly, the central processing unit reads continuously monitored expiratory-related data via its input ports during the execution of the ventilatory loop illustrated at "B".

An inspiratory breathing cycle program loop and control time for executing the loop are then entered as shown at 508. Once the inspiratory breathing cycle loop is entered, the aforementioned LCS, GCS and TCS values are read from the central processing unit's input ports as shown at 510 from "A". During the inspiratory breathing cycle, the central processing unit is designed to disregard the monitored expiratory breathing cycle data from "B".

The next step is to compare the actually monitored values during inspiration to their respective upper and lower limits which were programmed into the central processing unit by a medical practitioner as shown at 512. If any of the actual values are outside of their respective specified range, the central processing unit is designed to generate a signal. This signal can be sent to an alarm device as shown at 514 and/or to a servo-controlled valving network as shown at 516. In either instance, the appropriate adjustments are made in order to rectify the error as shown at 518.

If all monitored values are within their respective specified ranges (or after the appropriate adjustments have been made), it is necessary to determine whether there has been an expiratory breathing cycle as shown in step 520. If the answer is "No", the expiratory breathing cycle is initiated.

The liquid ventilation procedure then enters an expiratory breathing cycle program loop as shown at 522. Once the expiratory breathing cycle is entered, the aforementioned LCS, GCS and TCS values are read from the central processing unit's input ports as shown at 510 from "B". During the expiratory breathing cycle, the central processing unit is designed to disregard the monitored inspiratory breathing cycle data from "A".

The next steps are the same as those performed during the inspiratory breathing cycle (i.e., steps 512–520). However, after the expiratory breathing cycle is completed, the answer to step 520 will now be "YES". Under these circumstance, the next step is to determine whether the liquid ventilation procedure is completed as shown in 524.

If the answer is "NO", the inspiratory breathing cycle program loop at 508 is again initiated. However, if the answer is "YES", this means that the liquid ventilation process has achieved its desired goal. Accordingly, the next step is to terminate the liquid ventilation process and simultaneously replace it with a gas ventilation process as illustrated at 526.

In this preferred embodiment, the liquid ventilation conditions are monitored continuously and adjusted instantaneously. Therefore, the amount of time that a patient is subjected to a less than optimum conditions is minimal.

Another advantage to employing a Central Processing Unit (CPU) is that it can be programmed to consider the effects of atmospheric conditions and the presence of other tracer gases, if any. By monitoring the presence of tracer gases, the CPU can be programmed to determine parameters such as oxygen consumption, carbon dioxide production, respiratory quotient, cardiac output, pulmonary blood flow, diffusional dead space, anatomic dead space, intra- and extrapulmonary shunts, diffusion capacity and lung tissue water.

A specific example as to how a CPU can be interfaced to guide, monitor and regulate the system parameters of the LCS, the GCS and the TCS in accordance with this present invention is provided in FIGS. 9–11, respectively. For simplicity reasons, each figure is directed to only one control system. However, it is to be understood that the method of this invention incorporates all three of these systems together.

Referring now to FIG. 9, this Figure illustrates one embodiment of a LCS encompassed by the present invention. Specifically, in this embodiment, during inspiration, liquid is circulated by a pump 10 from an inspiratory liquid reservoir 11 through inspiratory valve 12 to patient 14 via line 15. Here, valve 12, in combination with pump 10, determine the following parameters associated with the inspiratory liquid delivered to the patient during the inspiration cycle: inspiratory liquid flow rate, inspiratory time, peak inflation pressures, inspiratory tidal volume, inspiratory lung volume and inspiratory breathing frequency.

The aforementioned parameters are continually monitored by pressure, flow and volume sensors which are collectively referred to as "inspiratory sensors 16". Inspiratory sensors 16 send the monitored information to CPU 50 via line 17.

Pre-determined inspiratory reference data associated with the above-identified parameters are input into CPU 50 by medically-skilled professionals via line 18. CPU 50 is designed to compare the information input therein from inspiratory sensors 16 via line 17 to the pre-determined inspiratory reference data input therein via line 18. After making this comparison, CPU 50 is designed to determine whether there is an error between the pre-determined inspiratory reference data parameters and the actually-occurring inspiratory values. If an error exists, CPU 50 is designed to effectuate the necessary adjustments.

There are a number of different ways in which CPU 50 can be designed to make these adjustments. These would be readily apparent to those skilled in the art upon reading this disclosure.

The overall goal of CPU 50 is to maintain the most effective gas exchange and cardiovascular function within preset limits while minimizing pressure-related pulmonary and cardiovascular compromise. Specifically, as shown in FIGS. 1–7, each parameter (e.g., pressure, flow, volume, etc.) is appropriately adjusted to be maintained within a predetermined range.

In explaining one example as to how the LCS illustrated in FIG. 9 can be designed to correct an error which may result, consider FIG. 4. As explained earlier, FIG. 4 is a volume vs. pressure loop illustrating the presence of overdistintention pressure. Specifically, FIG. 4 shows excessive pressurization of the lungs as represented by flattening of the pressure-volume loop. There, although lung and tidal volumes are within their respective pre-determined range, airway and alveolar pressure maximums are exceeded. Therefore, to reduce pressure and maintain lung and tidal volumes within their pre-determined range, inspiratory liquid flow should be reduced and inspiratory time should be increased according to mathematical algorithms which interrelate airway and alveolar pressures with liquid flow, respiratory resistance, respiratory compliance and inspiratory time.

If the situation illustrated in FIG. 4 is observed, the LCS illustrated in FIG. 9 can be designed to effectuate the necessary changes. For example, under these circumstances, CPU 50 can be designed to generate signals which manipulate pump 10 and valve 12 via lines 19 and 20, respectively. CPU 50 can then be designed to determine whether the adjustments have been effective in bringing the actually-occurring pressures and volumes within desired their pre-determined ranges by monitoring the signal's input therein via line 17 from inspiratory sensors 16.

In addition, certain of the patient's cardiovascular and gas exchange parameters are also preferably monitored. In the LCS illustrated in FIG. 9, such parameters are continually monitored by sensors which are collectively referred to as "cardiovascular sensors 21". The information monitored by cardiovascular sensors 21 is input into CPU 50 via line 22.

Also in the LCS illustrated in FIG. 9, CPU is designed to compare the pre-determined inspiratory reference values input therein via line 18 with the cardiovascular and gas exchange values input therein via line 22. This comparison is made to determine whether the mechanical changes, resulting from signals generated along lines 19 and 20, have influenced the patient's cardiopulmonary function.

During expiration, liquid is circulated by pump from patient 14 through expiratory valve 25 to expiratory liquid reservoir 26 via line 27. Here, valve 25, in combination with pump 24, determine the following parameters associated with the expiratory liquid removed from the patient during the expiration cycle: expiratory liquid flow rate, expiratory time, peak deflation pressures, expiratory tidal volume, expiratory lung volume and expiratory breathing frequency.

The aforementioned parameters are continually monitored by pressure, flow and volume sensors which are collectively referred to as "expiratory sensors 27". Expiratory sensors 27 send the monitored information to CPU 50 via line 28.

Pre-determined expiratory reference data associated with the above-identified parameters are input into CPU 50 by medically-skilled professionals via line 29. CPU 50 is designed to compare the information input therein from expiratory sensors 27 via line 28 to pre-determined expiratory reference data input therein via line 29. After making this comparison, CPU 50 is designed to determine whether there is an error between the pre-determined expiratory reference data parameters and the actually-occurring expiratory values. If an error exists, CPU 50 is designed to effectuate the necessary adjustments.

As indicated before, there are a number of different ways in which CPU 50 can be designed to make these adjustments. These would be readily apparent to those skilled in the art upon reading this disclosure.

In explaining another example as to how the LCS illustrated in FIG. 9 can be designed to correct an error which may result, consider FIG. 5A. As explained earlier, FIG. 5A is a volume vs. pressure loop illustrating the presence of an airway collapse. Specifically, FIG. 5A shows excessive negative pressurization of the lungs as represented by flattening of the pressure-volume loop. There, although tidal volume is within its pre-determined range, airway and alveolar pressure minimums are exceeded. Therefore, to reduce pressure and maintain tidal volume within its pre-determined range, expiratory liquid flow should be reduced and expiratory time should be increased according to mathematical algorithms which interrelate airway and alveolar pressures with liquid flow, respiratory resistance, respiratory compliance and expiratory time.

If the situation illustrated in FIG. 5A is observed, the LCS illustrated in FIG. 9 can be designed to effectuate the necessary changes. For example, under these circumstances, CPU 50 can be designed to generate signals which manipulate pump 24 and valve 25 via lines 30 and 31, respectively. CPU 50 can then be designed to determine whether the adjustments have been effective in bringing the actually-occurring pressures and volume within their desired pre-determined ranges by monitoring the signal's input therein via line 28 from expiratory sensors 27.

Since lung volume and tidal volume can influence cardiovascular function, another level of control performed by CPU 50 involves a feedback between cardiopulmonary and ventilatory parameters. Specifically, in the embodiment illustrated in FIG. 9, lung volume and tidal volume are continuously monitored by inspiratory sensors 16, expiratory sensors 28, sensor 32 and sensor 33. This monitored information is fed back into CPU 50 via lines 17, 28, 34 and 35, respectively.

As indicated earlier, CPU 50 is designed to compare the patient's cardiovascular and gas exchange parameters monitored by cardiovascular sensors 21 with expiratory reference data and inspiratory reference data. By making this comparison, CPU 50 can determine if lung volume or tidal volume changes have influenced the patient's cardiopulmonary function.

For example, if the patient's cardiovascular function is impaired by excessive lung volumes (e.g., increased lung volume, increases pulmonary vascular resistance, decreases right ventricular output, etc.), CPU 50 can be designed to measure an error in cardiovascular function and generate an appropriate signal which will correct this error. Specifically, under the aforementioned circumstances, CPU 50 can be designed to generate a signal to correct the excessive lung volume by manipulating pump 10, valve 20, pump 24 and valve 25 via lines 19, 20, 30 and 31, respectively. If manipulated properly, this will correct the excessive lung volume by reducing inspiratory flow rate, increasing expiratory time and increasing inspiratory time.

After these adjustments are made, CPU 50 can be designed to determine whether the adjustments have been effective in bringing the patient's cardiovascular function within the desired pre-determined expiratory reference data ranges and inspiratory reference data ranges input therein via lines 29 and 18, respectively. In addition, CPU 50 can be designed to compare expiratory reference data and inspiratory reference data input therein via lines 29 and 18, respectively, to the values monitored by inspiratory sensors 16, expiratory sensors 27, sensor 32 and sensor 33 as a means of determining whether lung volume changes have influenced the patient's cardiopulmonary function.

It should be noted that lung volume can indirectly influence oxygenation by compromising the patient's cardiopulmonary function. Lung volume can also directly influence oxygenation due to increased surface area for gas exchange.

In a similar feedback control algorithm as described above, lung volume can be increased or decreased to effectively change arterial oxygenation independent of the GCS. A detailed explanation of a GCS designed in accordance with the present invention will be described later when explaining FIG. 10.

Moreover, in addition to optimizing gas exchange through adjustments in lung mechanics and ventilatory parameters (i.e., tidal volumes, pressures, etc.), gas exchange can be optimized by measuring the carbon dioxide tension in the alveolar and mixed expiratory liquid using sensor 36. The information monitored by sensor 36 is fed into CPU 50 via line 37.

Under these circumstances, CPU 50 can be designed to compute diffusion dead space according to mathematical algorithms and optimize the respiratory frequencies and tidal volumes. CPU 50 can be designed to make any necessary adjustments at the end of expiration by manipulating pump 10, valve 12, pump 24 and valve 25 via lines 19, 20, 30 and 31, respectively.

After making these manipulations, CPU 50 can be designed to determine whether the adjustments have been effective in bringing carbon dioxide tension levels within the pre-determined levels. In addition, CPU 50 can be designed to compare expiratory reference data and inspiratory reference data input therein via lines 29 and 18, respectively, with values monitored by cardiovascular sensors 21 to determine if ventilatory changes have influenced the patient's cardiopulmonary function.

Referring now to FIG. 10, this Figure illustrates one embodiment of a GCS encompassed by the present invention. Specifically, in this embodiment, oxygen, carbon dioxide and nitrogen are fed into a gas manifold 100 via lines 102, 104 and 106, respectively. If desired, an inert tracer gas can optionally be fed into gas manifold 100 via line 108.

Gas manifold 100 includes a series of valves (not shown) which control the concentration of each gas passing therefrom into gas blender 110 via line 112. Blender 110 mixes the gases into a homogeneous mixture and passes them to the gas-liquid exchanger generally identified as 114.

Gas-liquid exchanger 114 has a gas inlet portion 118 and a liquid inlet portion 120. Moreover, gas-liquid exchanger 114 also includes a pump 122 which controls the flow of gas from gas inlet portion 118 into liquid inlet portion 120 and vice-versa.

An oxygen sensor 124 is positioned in gas liquid exchanger gas inlet portion 118. Sensor 124 monitors the oxygen concentration in the gas passing through the gas-liquid exchanger gas inlet portion 118 (i.e., the concentration of oxygen in the gas circuit).

Gas-liquid exchanger liquid inlet portion 120 also has an oxygen sensor 126 positioned therein. Sensor 126 monitors the concentration of oxygen in the liquid passing through gas-liquid exchanger liquid inlet portion 120 (i.e., the concentration of oxygen in the liquid circuit).

The signals generated by oxygen sensors 120 and 126 are passed to analyzers 128 and 130 via lines 132 and 134, respectively. A reference oxygen level is also passed into analyzers 128 and 130 via lines 136 and 138, respectively.

The reference oxygen level passed into analyzer 128 is the pre-determined value relating to the oxygen concentration level within the gas circuit. Similarly, the reference oxygen level passed into analyzer 130 is the pre-determined value relating to the oxygen concentration level within the liquid in the liquid circuit.

Analyzers 128 and 130 assess the error between sensors 124 and 126 and their respective reference oxygen concentration levels. This information is then fed into central processing unit (CPU) 50.

CPU 50 is programmed to make the necessary adjustments in order for the oxygen levels within the gas inlet portion 118 and liquid inlet portion 120 of gas-liquid exchanger 114 to be equal to their respective reference oxygen levels. There are a number of ways in which CPU 50 can be programmed to make these adjustments. For example, a signal can be sent to flow controller 142.

Flow controller 142 is linked with pump 122 of gas-liquid exchanger 114. As stated earlier, pump 122 controls the flow of fluids from gas inlet portion 118 to liquid inlet portion 120 and vice versa. Therefore, by appropriately adjusting the flow of fluids therebetween, the oxygen concentration levels within the respective inlet portions can also be adjusted.

Another method in which CPU 50 can control the level of oxygen contained within the gas passing through gas inlet portion 118 and liquid passing through liquid inlet portion 120 is by sending an appropriate signal to gas manifold 100 via line 144. This signal can be designed to adjust the valve controlling the amount of oxygen passing from manifold 100 into gas blender 110. This would alter the concentration of oxygen within the gas passing through gas inlet portion 118 and liquid inlet portion 120.

As stated above, the third sub-level of control in the GCS guides, monitors and regulates the gas levels within the patient. In this sub-level of control, an oxygen sensor 146 is generally placed in an appropriate region of the patient's circulatory system.

Oxygen sensor 146 monitors the concentration of oxygen within the patient's blood during the liquid ventilation process. This information is passed to analyzer 148 via line 150. A signal representing the reference oxygen level relating to the patient's blood is also fed into analyzer 148 via line 152.

Analyzer 148 assesses the error between the oxygen level monitored by sensor 146 and that supplied via line 152. This information is transmitted to CPU 50 which adjusts the liquid ventilation system accordingly.

As stated above, there are many different ways in which CPU 50 can be programmed to correct errors in oxygen concentration levels within the patient. One method is by controlling the oxygen concentration of the gas as it passes through gas blender 110. Another method is by controlling the mixing of oxygenated gas and breathing liquid in gas-liquid exchanger 114 via flow control means 142 and pump 122. Yet another method is by controlling certain aspects of the LCS. The actual adjustments which will be made will depend, in part, upon the patient's optimum volume vs. pressure loop and the patient's optimum flow vs. volume loop as described earlier.

For example, CPU 50 can be programmed to regulate the following parameters associated with the LCS: the rate at which oxygenated liquid passes through the patient's pulmonary pathways, the tidal lung liquid volume of the patient during the liquid ventilation procedure, the resting lung liquid volume of the patient during the liquid ventilation procedure, and the like. These adjustments, when performed singularly or collectively, will have an effect on the oxygen level within the patient.

The GCS can also be designed to monitor and/or regulate the amount of oxygen and/or carbon dioxide in the expired breathing liquid. This information is extremely useful when determining the efficiency of gas exchange between the oxygenated breathing liquid and the patient.

In FIG. 10, expired breathing liquid passes from the patient via line 154. A sensor 156 is positioned to monitor gas concentrations within the expired breathing liquid. This monitored information is fed into CPU 50 via line 158.

Based, in part, on the information received from sensor 156, CPU 50 can control the amount of expired breathing liquid recycled to the liquid inlet portion 120 of gas-liquid exchanger 114. This degree of control can be performed by regulating valves 160 and 162 via signals generated by CPU 50 and passed thereto via lines 164 and 166, respectively.

Prior to being recycled into the gas-liquid exchanger 114, the expired breathing liquid passes through gas scrubber 168 which removes all undesired gases therefrom. After being scrubbed, the expired breathing liquid passes from gas scrubber 168 to the gas-liquid exchanger liquid inlet portion 120 via line 170.

Interposed between gas scrubber 168 and liquid inlet portion 120 is sensor 172. This sensor monitors the level of gases in the expired breathing liquid after passing through gas scrubber 168. Sensor 172 transmits the monitored information to CPU 50 via line 174. If there is unacceptable levels of undesired gases in the expired breathing liquid, CPU 140 can be programmed to make the necessary adjustments to the gas scrubbing procedure. This may include, for example, increasing gas scrubbing time and/or supplementing the amount of liquid being recycled with a fresh source of breathing liquid via line 173 and valve 175.

The GCS described in FIG. 10 is merely one embodiment in which this aspect of the invention can be practiced. Upon reading this disclosure, those skilled in the art would readily understand how to adjust this particular GCS in order to accommodate the specific needs of the patient and a specific liquid ventilation system.

Referring now to FIG. 11, this Figure illustrates one embodiment of a TCS encompassed by the present invention. In this embodiment, thermal sensors are used in both the internal and external section of the TCS. These sensors can take any suitable form (e.g., thermistors, thermocouples, radiant heat sources, etc.).

In FIG. 11, thermal sensor 202 is placed in the inspired liquid as it passes from the liquid/gas exchanger 204 into the patient via line 206. Moreover, sensor 208 is placed in the patient's esophagus; and, sensor 210 is placed in the patient's rectum. These two sensors monitor the core temperature of the patient's trunk 212.

A sensor 214 is also positioned adjacent to the patient's tympanic membrane. This sensor monitors core temperature of the patient's head 216.

A plurality of sensors, collectively referred to by item 218, are also placed on each of the patient's extremities, collectively referred to as item 220. These sensors are designed to monitor the patient's surface and peripheral body temperatures.

A temperature sensor 230 is placed into the breathable liquid source 232. This is designed to monitor the temperature of the breathable liquid prior to its entering the liquid/gas exchanger 204 via line 234. Also, sensor 236 is positioned in gas source 238. This is designed to monitor the temperature of the gas source prior to its entering liquid/gas exchanger 204 via line 240.

Sensor 242 is positioned in liquid/gas exchanger 204. This sensor is designed to monitor the temperature of the oxygenated gas prior to it being inspired by the patient.

In order to monitor the temperature of the expired breathing liquid, sensor 244 is positioned in expiratory liquid line 246. If the liquid passing through line 246 is to be recycled into the breathable liquid source 232, sensor 244 is interposed between the patient and breathable liquid source 232.

In addition to the above, sensors 222 and 224 are placed in the heating source 226 and cooling source 228, respectively.

Each of the aforementioned sensors are interlinked with CPU 50. CPU 50 is, in turn, interlinked with heating source 226 and cooling source 228 via output lines 248 and 250, respectively.

Heating source 226 and cooling source 228 comprise a series of valves which can be regulated to meter a specific amount of the heating or cooling means to breathing liquid source 232, gas source 238 and liquid/gas exchanger 204, as well as, the various parts of the patient's body (i.e., head 216, trunk 212 and/or extremities 220). CPU 50 is designed to control each of the heating source's valves through an output signal passing along line 248. Similarly, CPU 50 is also designed to control each of the cooling source's valves via an output signal passing along line 250.

In operation, sensor 202 monitors the temperature of the oxygenated gas passing from liquid/gas exchanger 204 into the patient via line 206. This mentioned information is fed into CPU 50 via line 252. If the temperature of the oxygenated breathing liquid passing by sensor 202 is not at its desired level, CPU 50 is designed to send a signal to heating source 226 or cooling source 228.

Specifically, if the temperature of the oxygenated breathing liquid passing through line 206 is below its desired temperature, CPU 50 will pass the appropriate signal to heating source 226 via line 248. This will open the appropriate valves necessary for heating source 226 to raise the temperature of the oxygenated breathing liquid to the correct level. This can be done by passing a heating liquid to breathable liquid source 232 via line 254, to gas source 238 via line 256 and/or to liquid/gas exchanger 204 via line 258.

Similarly, if the temperature of the oxygenated breathing liquid passing by sensor 202 is above its desired temperature range, CPU 50 will send the appropriate signal to cooling source 228 via output line 250. Here, the appropriate valves will be adjusted in order to properly regulate the oxygenated breathing liquid's temperature. Specifically, CPU 50 can regulate cooling source 228 such that a cooling fluid is passed to breathable liquid source 232 via line 260, to gas source 238 via line 262 and/or liquid/gas exchanger 204 via line 264.

In either of the above instances, sensors 230, 242 and 236 monitor the temperature within breathable liquid source 232, liquid/gas exchanger 204 and gas source 238, respectively. These sensors pass their monitored temperatures to CPU 50 via signal lines 266, 268 and 270, respectively.

As stated above, sensors 214, 208, 210 and 218 are positioned to monitor the patient's internal and external body temperature. These sensors are linked with CPU 50 via lines 272, 274, 276 and 278, respectively.

Figure 12C:
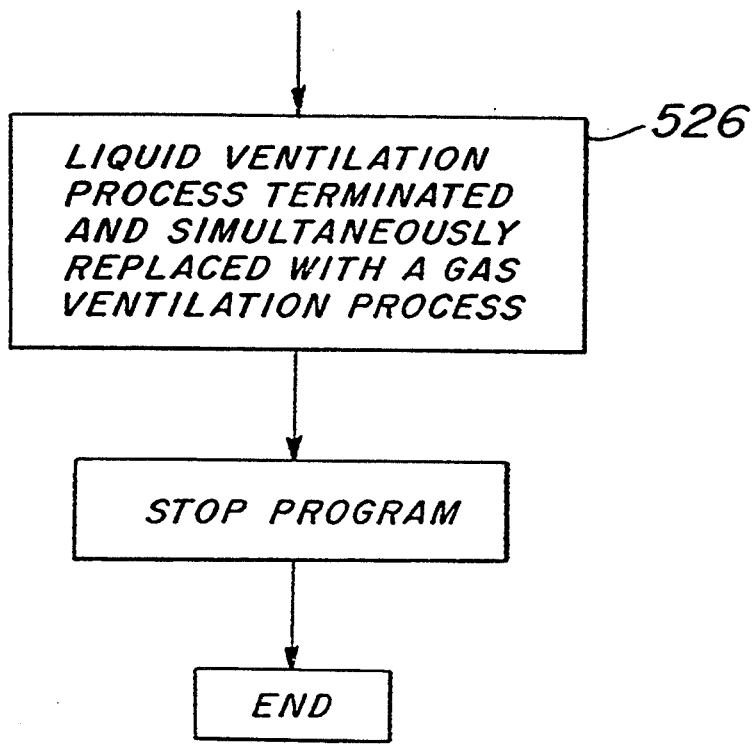

In the specific embodiment illustrated in FIG. 12, heating source 226 and cooling source 228 are designed to independently control the temperature in the patient's head 216, trunk 212 and extremities 220. Specifically, if either of sensors 214, 208 and 210, or 218 indicate that a particular region of the patient's body is below its desired temperature range, CPU 50 will, in turn, pass the appropriate signal to heating source 226 via output signal line 248. The signal passing through line 248 will adjust the heating source such that the appropriate heating solution will pass to the patient's head 216, the patient's trunk 212 or the patient's extremities 220 via lines 280, 282 or 284, respectively.

Similarly, if the sensors indicate that the patient's head, trunk and/or extremities are above their desired temperature range, CPU 50 will pass the appropriate signal to cooling source 228 via output signal line 250. This signal will adjust cooling source 228 such that the appropriate cooling solution will pass to the patient's head 216, trunk 212 or extremities 220 via lines 286, 288 or 290, respectively.

FIG. 11 illustrates but one method of guiding, monitoring and regulating a patient's internal and external body temperatures during a liquid breathing procedure. Upon reading this disclosure, those skilled in the art will be able to adapt this system accordingly depending upon the patient's specific needs and the specific liquid ventilation system employed.

It is also within the purview of this invention to employ the novel method disclosed herein as a means for delivering biological agents into a patient through the patient's pulmonary pathways.

While it is known that biological agents can be administered to parts of a patient's pulmonary pathways via an aerosol, this conventional technique has certain disadvantages associated therewith. For example, airway obstruction and poor compliance can alter the mechanical time constants and bulk flow properties in the lung and interfere with the distribution of aerosolized agents.

If these problems exist, another conventional procedure for delivering biological agents to a patient's pulmonary system is via systemic administration. However, this technique also has disadvantages associated therewith. For example, pulmonary vascular shunting can limit the delivery of systemically administered agents that are targeted for the lung.

Applicants have discovered that, in most instances, these problems are not encountered when delivering the biological agents into a patient's pulmonary pathways via a breathing liquid. Specifically, the pulmonary administration of biological agents is enhanced when mixed with a breathing liquid used for liquid ventilation/lavage procedures for the following reasons: (a) due to their low surface tension, breathing liquids are uniformly distributed and reach the terminal gas exchange regions in the lung; (b) pulmonary blood flow is more homogeneously distributed and ventilation/perfusion is more evenly matched in a liquid-filled lung; (c) breathing liquids can be selectively directed to specific regions of the lung; (d) gas exchange may be supported during the administration of the biological agents; and (e) biological inertness of many breathing liquids prevent possible side effects due to an interaction between the liquid vehicle and biological agent interaction.

In a presently preferred embodiment, the means for transporting these agents is by convective mass transport. This is most effective when these agents are thoroughly mixed with the breathing fluid.

In order to achieve effective mixing and convective transport, the agent is preferably injected into the breathing liquid at maximum flow conditions of the inspiratory period. More preferably, the agent is injected perpendicularly to the stream of breathing liquid.

The site of injection can be, for example, in the common line of the liquid ventilation and/or lavage system or in a specifically designed endotracheal tube. Moreover, the injection process can be done during a single breath or over a series of breaths. The latter will result in a time-released effect.

The injection unit can also be configured for sampling of lung exudate during expiration. Here, time-withdrawal of expired liquid samples during the appropriate phase of expiration are regulated in order to prevent dilution with fresh inspired breathing liquid.

As can be seen, this method of delivering biological agents into a patient can be incorporated with the control system disclosed herein. For example, the LCS, GCS and TCS can be designed to guide, monitor and regulate the amount of biological agent(s) introduced into the breathing liquid, the manner in which the agent(s) is/are introduced, and the effects of its/their introduction on the patient. The optimum way of modifying the control system disclosed herein depends upon the agent being introduced, the ventilation system, and the patient. Once these variables are known, skilled artisans will know how to make the necessary modifications after reading this disclosure.

It is also within the purview of this invention to employ the novel control system disclosed herein as a means for maintaining the patient's body temperature constant or for subjecting the patient to a hyper- or hypo-thermic treatment. Here, in addition to maintaining the patient's gas exchange, the breathing liquid can also be used as a means for obtaining a desired temperature. A specific example as to how temperature control can be achieved in accordance with the present invention is illustrated in FIG. 11 described above.

It is evident from the foregoing that various modifications can be made to the embodiments of this invention without departing from the spirit and/or scope thereof which would be apparent to those skilled in the art.

Having thus described the invention, it is claimed as follows:

1. A process for guiding, monitoring and regulating a liquid ventilation system wherein said ventilation system is designed to circulate a breathing liquid through at least a portion of a patient's pulmonary pathways, and wherein said liquid ventilation system includes a liquid circuit component, a gas circuit component and a temperature circuit component, said process comprising the steps of:
   (a) establishing a set of desired ranges for process parameters associated with the liquid circuit, the gas circuit and the temperature circuit components of said liquid ventilation system, correlating said set of established desired ranges to the physiological needs of the patient, and representing said set of established desired ranges by a first set of signals;
   (b) inputting the first set of signals in to a microprocessor;
   (c) establishing the patient's initial ventilatory profile by making initial adjustments to the liquid circuit, the gas circuit and the temperature circuit components of said liquid ventilation system such that actual conditions of said liquid ventilation system's liquid circuit, gas circuit and temperature circuit components, occurring while a breathing liquid circulates through at least a portion of said patient's pulmonary pathways, fall within the purview of their corresponding established desired ranges;
   (d) circulating a breathing liquid through at least a portion of said patient's pulmonary pathways in accordance with said patient's initial ventilatory profile;
   (e) monitoring a set of actual conditions of said liquid ventilation system's liquid circuit, gas circuit and temperature circuit components which occur while said breathing liquid is circulating through at least a portion of said patient's pulmonary pathways, and representing said set of monitored actual conditions by a second set of signals, said monitored set of actual conditions correspond with said set of established desired ranges;
   (f) inputting the second set of signals into said microprocessor
   (g) implementing said micro-processor to determine whether said second set of signals fall within the purview of their corresponding ranges represented by said first set of signals, and representing instances wherein said second set of signals fall outside of said first set of signals by a third set of signals; and
   (h) making subsequent adjustments to said patient's initial ventilatory profile by implementing said third set of signals such that said second set of signals fall within the purview of their corresponding ranges represented by said first set of signals.

2. A process in accordance with claim 1 further comprising the steps of:
   monitoring the breathing liquid's pressures, flow rates and volumes, as in step (e);
   deriving a second set of signals based upon said monitoring of the breathing liquid's pressures, flow rates and volumes;
   feeding said second set of signals based upon said monitoring of the breathing liquid's pressures, flow rates and volumes into the liquid circuit component of said liquid ventilation system; and
   regulating the circulation of a breathing liquid through at least a portion of said patient's pulmonary pathways with the liquid circuit component of said liquid ventilation system by utilizing information gained from the second set of signals based upon said monitoring of the breathing liquid's pressures, flow rates and volumes.

3. A process in accordance with claim 2 further comprising the steps of:
assessing the respiratory gas levels and tracer gas levels contained in samples of said breathing liquid before the breathing liquid is inspired by the patient and after the breathing liquid is expired by the patient; and
having the liquid circuit component of said liquid ventilation system utilize the information gained from the assessment of said breathing liquid's respiratory gas levels and tracer gas levels.

4. A process in accordance with claim 1 further comprising the steps of:
monitoring as in step (e) the inspiratory and expiratory gas levels contained in at least the following areas:
in samples of gases before they are blended with the breathing liquid,
in samples of the breathing liquid after it has been expired by said patient, and
in samples of blood taken from said patient's circulatory system while the breathing liquid is being circulated through at least a portion of said patient's pulmonary pathways;
deriving a second set of signals based upon said monitored inspiratory and expiratory gas levels;
feeding the second set of signals pertaining to said monitored inspiratory and expiratory gas levels back into the gas circuit component of said liquid ventilation system; and
regulating the partial pressures, tensions and concentrations of gases in the liquid ventilation system's gas circuit component and liquid circuit component, as well as in the patient, with the gas circuit component of said liquid ventilation system by utilizing information gained from the second set of signals based upon said monitored inspiratory and expiratory gas levels.

5. A process in accordance with claim 4 further comprising the steps of:
gaining information from an on-line assessment of tracer gases; and
determining at least one physiological parameter with the gas circuit component of said liquid ventilation system by utilizing information gained from an on-line assessment of tracer gases, said physiological parameter being determined is selected from the group consisting of: oxygen consumption, carbon dioxide production, respiratory quotient, cardiac output, effective pulmonary blood flow, diffusional dead space, anatomic dead space, intrapulmonary and extrapulmonary shunts, diffusional capacity and lung tissue water.

6. A process in accordance with claim 1 further comprising the steps of:
monitoring the patient's internal and external body temperatures while said breathing liquid is being circulated through at least a portion of said patient's pulmonary pathways as in step (e);
deriving a second set of signals based upon the monitoring of said patient's internal and external body temperatures;
feeding the second set of signals based upon the monitoring of said patient's internal and external body temperatures back into the temperature circuit component of said liquid ventilation system; and
regulating the patient's internal and external body temperatures while said breathing liquid is being circulated through at least a portion of said patient's pulmonary pathways with the temperature circuit component of said liquid ventilation system by utilizing information gained from the second set of signals based upon the monitoring of said patient's internal and external body temperatures.

7. A process in accordance with claim 1 further comprising the step of:
making at least the following initial adjustments to the liquid circuit, gas circuit and temperature components of the liquid ventilation system during step (c): a starting lung liquid volume, the breathing liquid's initial pressure, initial tidal lung liquid volume, the breathing liquid's initial flow rate, an initial concentration of oxygen in a specific volume of said breathing liquid prior to said breathing liquid being inspired by said patient, a resting lung liquid volume, a peak inspiratory air way pressure, a peak expiratory air way pressure, a peak alveolar pressure, a peak esophageal pressure, an initial breathing frequency, a timing ratio of inspiratory-to-expiratory liquid flow, the patient's core body temperature, and the temperature of the breathing liquid prior to it being inspired by said patient.

8. A process in accordance with claim 1 further comprising the step of:
making the initial adjustments to the liquid circuit, gas circuit and temperature components of the liquid ventilation system during step (c) such that the actual conditions of the liquid ventilation system's liquid circuit, gas circuit and temperature circuit components, monitored in step (e), fall within the following ranges: a starting lung liquid volume ranging from between about 20 to about 30 ml/kg, the breathing liquid's initial pressure ranging from between about −50 to about 50 $cmH_2O$, a tidal lung liquid volume ranging from between about 10 to about 20 ml/kg, the breathing liquids initial flow rate ranging from between about −300 to about 300 ml/min/kg, an initial concentration of oxygen in a specific volume of breathing liquid ranging from between about 100 to about 600 mmHg, a resting lung liquid volume ranging from between about 20 to about 40 ml/kg, a peak inspiratory airway pressure ranging from between about 80 to about 100 $cmH_2O$, a peak expiratory airway pressure ranging from between about −80 to about −100 $cmH_2O$, peak alveolar and esophageal pressures ranging from between about 15 to about 20 $cmH_2O$, a breathing frequency ranging from between about 3 to about 8 breaths per minute, a timing ratio of inspiratory-to-expiratory gas ranging from between about 1:2 to about 1:4, the patient's core body temperature ranging from between about 25° to about 39° C., and the breathing liquid's temperature, prior to it being inspired by said patient, ranging from between about 20° to about 42° C.

9. A process in accordance with claim 1 further comprising the step of:
establishing minimum and maximum values for at least the following parameters associated with the liquid circuit component of said liquid ventilation system in step (a): the breathing liquid's pressure for when it is being circulated through at least a portion of said patient's pulmonary pathways, the breathing liquid's tidal lung liquid volume for when it is being circulated through at least a portion of said patient's pulmonary pathways, the breathing liquid's resting lung liquid volume for when it is being circulated through at least a portion of said patient's pulmonary pathways, the breathing liquid's flow rate for when it is being circulated through at least a portion of said patient's pulmonary pathways, an amount of oxygen to be absorbed by the patient from a specific volume of said breathing liquid as said breathing liquid is being circulated through at least a portion of said patient's pulmonary pathways, and an amount of carbon dioxide to be absorbed from said patient by a specific volume of said breathing liquid as said breathing liquid is being circulated through at least a portion of said patient's pulmonary pathways.

10. A process in accordance with claim 1 further comprising the step of:

establishing minimum and maximum values for at least the following parameters associated with the gas circuit component of said liquid ventilation system in step (a): a concentration of oxygen in a specific volume of gas being blended with said breathing liquid, a concentration of oxygen in a specific volume of said breathing liquid prior to said breathing liquid is inspired by said patient, a concentration of oxygen in a specific volume of said breathing liquid after said breathing liquid is expired by said patient, a concentration of carbon dioxide in a specific volume of said breathing liquid after said breathing liquid is expired by said patient, and a concentration of oxygen in said patient's circulatory system while said breathing liquid is being circulated through at least a portion of said patient's pulmonary pathways.

11. A process in accordance with claim 1 further comprises the step of:

establishing minimum and maximum values for at least the following parameters associated with the temperature circuit component of said liquid ventilation system in step (a): the breathing liquid's temperature prior to said breathing liquid being inspired by said patient, the patient's internal body temperature while said breathing liquid is being circulated through at least a portion of said patient's pulmonary pathways, and the patient's external body temperature of while said breathing liquid is being circulated through at least a portion of said patient's pulmonary pathways.

* * * * *